United States Patent
Fulp et al.

(10) Patent No.: US 9,133,128 B2
(45) Date of Patent: Sep. 15, 2015

(54) PYRAZOLE DERIVATIVES AS CANNABINOID RECEPTOR 1 ANTAGONISTS

(75) Inventors: Alan Bradley Fulp, Willow Spring, NC (US); Rangan Maitra, Cary, NC (US); Yanan Zhang, Apex, NC (US); Herbert H. Seltzman, Raleigh, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 14/126,194

(22) PCT Filed: Jun. 15, 2012

(86) PCT No.: PCT/US2012/042640
§ 371 (c)(1),
(2), (4) Date: Dec. 13, 2013

(87) PCT Pub. No.: WO2012/174362
PCT Pub. Date: Dec. 20, 2012

(65) Prior Publication Data
US 2014/0107157 A1 Apr. 17, 2014

Related U.S. Application Data

(60) Provisional application No. 61/498,270, filed on Jun. 17, 2011.

(51) Int. Cl.
*C07D 231/14* (2006.01)
*A61K 31/415* (2006.01)
*C07D 401/06* (2006.01)
*C07D 401/12* (2006.01)

(52) U.S. Cl.
CPC ............ *C07D 231/14* (2013.01); *A61K 31/415* (2013.01); *C07D 401/06* (2013.01); *C07D 401/12* (2013.01)

(58) Field of Classification Search
None
See application file for complete search history.

(56) References Cited

U.S. PATENT DOCUMENTS

| | | | |
|---|---|---|---|
| 3,449,350 A | 6/1969 | Walker | |
| 5,624,941 A | 4/1997 | Barth et al. | |
| 6,825,209 B2 * | 11/2004 | Thomas et al. | 514/285 |
| 7,659,407 B2 | 2/2010 | Lazzari et al. | |
| 2007/0213302 A1 | 9/2007 | McElroy et al. | |
| 2008/0153867 A1 | 6/2008 | Lange et al. | |
| 2009/0069329 A1 | 3/2009 | McElroy et al. | |

FOREIGN PATENT DOCUMENTS

| | | |
|---|---|---|
| EP | 1 878 723 | 1/2008 |
| WO | WO 2007/138277 | 12/2007 |

OTHER PUBLICATIONS

Cooper et al., "Exploring SAR Features in Diverse Library of 4-Cyanomethyl-Pyrazole-3-Carboxamides Suitable for Further Elaborations as CB1 Antagonists," *Bioorg. Med. Chem. Lett.*, 2010, pp. 26-30, vol. 20.

Database Registry, Chemical Abstracts Service, May 4, 2011, CAS Registry No. 1289702-40-4.
Database Registry, Chemical Abstracts Service, Apr. 13, 2011, CAS Registry No. 1279227-80-3.
Fang et al., "A General Modular Method of Azaindole and Thienopyrrole Synthesis via Pd-Catalyzed Tandem Couplings of gem-Dichloroolefins," *J. Org. Chem.*, 2007, pp. 5152-5160, vol. 72.
Fulp et al., "Towards Rational Design of Cannabinoid Receptor 1 (CB1) Antagonists for Peripheral Selectivity," *Bioorganic & Medicinal Chemistry Letters*, 2011, pp. 5711-5714, vol. 21.
Fulp et al., "Design and Synthesis of Cannabinoid Receptor 1 Antagonists for Peripheral Selectivity," *Journal of Medicinal Chemistry*, 2012, pp. 2820-2834, vol. 55.
Hortala et al., "Rational Design of a Novel Peripherally-Restricted, Orally Active $CB_1$ Cannabinoid Antagonist Containing a 2,3-diarylpyrrole Motif," *Bioorg. Med. Chem. Lett.*, 2010, pp. 4573-4577, vol. 20.
Huang et al., "Excellent Correlation Between Substituent Constants and Pyridinium N-methyl Chemical Shifts," *Tetrahedron Letters*, 2009, pp. 5018-5020, vol. 50, No. 35.
Loverme et al., "Synthesis and Characterization of a Peripherally Restricted $CB_1$ Cannabinoid Antagonist, URB447, that Reduces Feeding and Body-Weight Gain in Mice," *Bioorg. Med. Chem. Lett.*, 2009, pp. 639-643, vol. 19.
Receveur et al., "Conversion of 4-cyanomethyl-pyrazole-3-carboxamides into CB1 Antagonists with Lowered Propensity to Pass the Blood-Brain-Barrier," *Bioorg. Med. Chem. Lett.*, 2010, pp. 453-457, vol. 20.
Reggio, "Pharmacophores for Ligand Recognition and Activation/Inactivation of the Cannabinoid Receptors," *Current Pharmaceutical Design*, 2003, pp. 1607-1633, vol. 9.

(Continued)

*Primary Examiner* — Timothy R Rozof
(74) *Attorney, Agent, or Firm* — Womble Carlyle Sandridge & Rice, LLP

(57) ABSTRACT

The invention provides compounds capable of acting as antagonists at cannabanoid receptors according to the following formula: Such compounds may be used to treat conditions for which the cannabinoid receptor system has been implicated, such as obesity, liver disease, diabetes, pain, and inflammation.

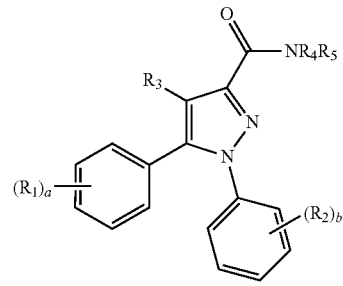

8 Claims, No Drawings

(56) References Cited

OTHER PUBLICATIONS

Sasmal et al., "Novel Pyrazole-3-Carboxamide Derivatives as Cannabinoid-1 (CB1) antagonists: Journey From Non-Polar to Polar Amides," *Bioorg. Med. Chem. Lett.*, 2011, pp. 562-568, vol. 21.

Seltzman et al., "Tritiation of SR141716 by Metallation-iodination-reduction: Tritium-proton nOe Study," *Journal of Labelled Compounds and Radiopharmaceuticals*, 2002, pp. 59-70, vol. 45.

Tam et al., "Peripheral CB1 Cannabinoid Receptor Blockade Improves Cardiometabolic Risk in Mouse Models of Obesity," *The Journal of Clinical Investigation*, 2010, pp. 2953-2966, vol. 120, No. 8.

Zhang et al. "Conformationally Constrained Analogues of N-(Piperidinyl)-5(4-Chlorophenyl)-1-(2,4-Dichlorophenyl)-4-Methyl-1H-Pyrazole-3-Carboxamide (SR141716): Design, synthesis, Computational Analysis, and Biological Evaluations," *J. Med. Chem.*, 2008, vol. 51, pp. 3526-3539.

Zhang et al. "Synthesis and Biological Evaluation of Bivalent Ligands for the Cannabinoid 1 Receptor," *J Med. Chem.*, 2010, pp. 7048-7060, vol. 53.

* cited by examiner

PYRAZOLE DERIVATIVES AS CANNABINOID RECEPTOR 1 ANTAGONISTS

CROSS-REFERENCE TO RELATED APPLICATIONS

The present application is a U.S. National Stage of International Patent Application PCT/US2012/042640, filed Jun. 15, 2012, and claims priority to U.S. Provisional Patent Application No. 61/498,270, filed Jun. 17, 2011, the disclosures of which are incorporated herein by reference in their entirety.

FEDERALLY SPONSORED RESEARCH OR DEVELOPMENT

This invention was made with United States Government support under Research Grants 1R21AA019740 and 1R03AA017514, awarded by the National Institutes of Health's National Institute on Alcohol Abuse and Alcoholism. The United States Government has certain rights in the invention.

FIELD OF THE INVENTION

The present application is directed to various compounds and methods of preparation of compounds that are capable of functioning as cannabinoid receptor 1 (CB1) antagonists. The application is also directed to pharmaceutical compositions containing one or more of these compounds, which may also contain one or more additional therapeutic agents. It is also directed to methods of treatment of various conditions that may be responsive to antagonism of the CB1 receptors, including, but not limited to, metabolic syndromes (including liver disease, obesity, and diabetes).

BACKGROUND OF THE INVENTION

Cannabinoid receptors (CBRs) belong to the endocannabinoid (EC) system, which consists of receptors, transporters, endocannabinoids, and enzymes involved in synthesis and degradation of endocannabinoids. The EC system regulates many important physiological processes and several components of the EC system are under evaluation as targets to treat a diverse array of indications including obesity, liver disease, diabetes, pain and inflammation. To date, two different cannabinoid receptors have been identified (referred to as CB1 and CB2). CB1 and CB2 receptors fall within the class of G protein-coupled receptors, and primarily function to activate inhibitory G proteins (Gi/o).

The CB1 receptor is prominently expressed in the central nervous system (CNS) and also in peripheral tissues. Accordingly, drugs targeting the CB1 receptors have been developed over the years to treat various metabolic disorders including obesity and diabetes. The first drug selective for CB1 that was developed for medical use was rimonabant, an inverse agonist/antagonist. Rimonabant was designed to treat obesity and other related disorders that have both CNS and peripheral components. However, rimonabant was withdrawn from European markets and denied FDA approval in the United States due to CNS-related side effects including anxiety, depression and suicidal ideation. The development of other related compounds (e.g., taranabant, otenabant, and ibipinabant) was discontinued based on these noted side effects. Accordingly, it would be beneficial to provide CB1 antagonists that are effective, but that do not result in such CNS-related side effects.

SUMMARY OF THE INVENTION

The present invention provides compounds useful as antagonists of the CB1 receptor and methods of synthesis of such compounds. In certain embodiments, peripherally restricted compounds that do not cross the blood-brain barrier have been developed in an effort to maintain the ability to block the CB1 receptor while minimizing CNS-related side effects noted with CB1 antagonists.

It also provides pharmaceutical compositions containing the compounds, which may be useful in the treatment of various conditions and/or disorders responsive to the antagonism of CB1 receptors. The invention further provides methods of treating such conditions and/or disorders, including but not limited to, metabolic disorders including liver disease, obesity, and diabetes. For example, in one aspect, the present invention is directed to a method of treating a condition comprising administering to a subject in need of treatment of the condition a pharmaceutical composition comprising a therapeutically effective amount of a compound of the present invention or a pharmaceutically acceptable ester, amide, salt, solvate, prodrug, or isomer thereof.

Accordingly, in one aspect, the present invention provides a compound that acts as an antagonist at CB1 receptors. In some embodiments, the invention provides a compound according to the following structure:

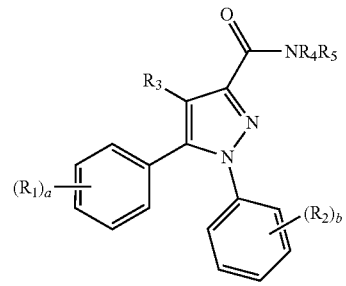

wherein:

each $R_1$ and $R_2$ is a substituent independently selected from the group consisting of Cl, F, Br, OH, optionally substituted C1-10 alkyl, optionally substituted C1-10 alkoxy, optionally substituted C2-4 alkenyl, optionally substituted C1-4 alkynyl, $NR_{10}R_{11}$, $NHCOR_{10}$, $NHCO_2R_{10}$, $CH_2OR_{10}$, $CONR_{10}R_{11}$, $CO_2R_{10}$, CN, $CF_3$, $NO_2$, $N_3$, C1-3 alkylthio, $R_{10}SO$, $R_{10}SO_2$, $CF_3S$, and $CF_3SO_2$;

$R_3$ is H or C1-3 alkyl;

$R_4$ is H or C1-10 alkyl;

$R_5$ is selected from:

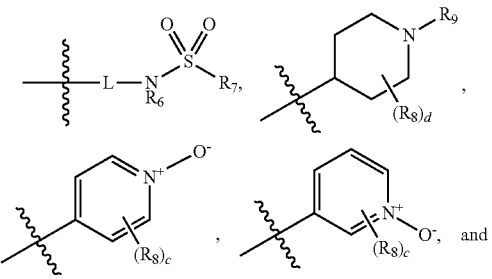

-continued

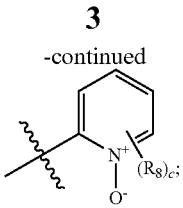

or R₄ and R₅ taken together form a piperidine ring with the N to which they are attached, which is substituted at the 4 position with one or two substituents selected from the group consisting of OH, optionally substituted aryl (e.g., phenyl), $NR_{10}R_{11}$, $NR_{10}COR_{11}$, $NR_{10}SO_2R_{11}$, $NHCONR_{10}R_{11}$, $NR_{10}COOR_{11}$; and $CONR_{10}R_{11}$, $R_6$ is H or C1-10 alkyl;
$R_7$ is C1-10 alkyl, $NR_{10}R_{11}$, or $NR_{10}COR_{11}$;
$R_8$ is C1-10 alkyl;
$R_9$ is H, C1-10 alkyl, acyl, amido, acylamido, $SO_2R_{10}$, $CONR_{10}R_{11}$, or $COOR_{10}$;
$R_{10}$ and $R_{11}$ are independently selected from H and C1-10 alkyl;
L is a linker, selected from:
  optionally substituted C1-15 alkyl and C1-15 heteroalkyl, wherein the alkyl or heteroalkyl may comprise one or more cycloalkyl or cycloheteroalkyl rings;
  optionally substituted alkylaryl;
  optionally substituted arylalkyl; and
  optionally substituted alkylarylalkyl;
a and b are each independently integers from 0 to 5; and
c is an integer from 0 to 4;
d is an integer from 0 to 8;
or a pharmaceutically acceptable ester, amide, salt, solvate, prodrug, or isomer thereof.

In certain embodiments, a is 1 and the $R_1$ substituent is at the para position and b is 2 and the $R_2$ substituents are at the ortho and para positions. In some embodiments, $R_1$ and both $R_2$ substituents are Cl. In certain embodiments, $R_3$ is $CH_3$. In some embodiments, $R_4$ is H.

In one embodiment, L can comprise, for example, a cyclohexyl group. For example, L can be $CH_2$—$C_6H_{10}$—$CH_2$. In certain embodiments, L can comprise an unsubstituted straight chain alkyl group (e.g., a C7 alkyl). In certain embodiments, L can comprise a number of carbon atoms in sequence between $NR_4$ and $NR_6$ that is greater than 4 carbon atoms, greater than 5 carbon atoms, or greater than 6 carbon atoms. In certain embodiments, $R_6$ is H. In certain embodiments, $R_7$ is selected from $CH_3$ and $NH_2$.

In some embodiments, a compound is provided according to the following structure:

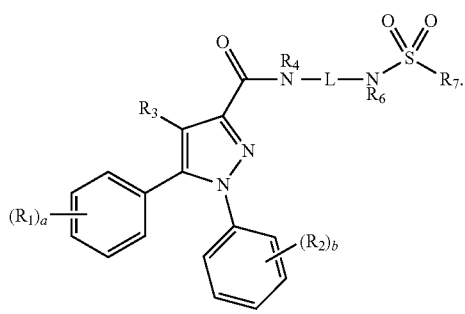

In some embodiments, a compound is provided according to the following structure:

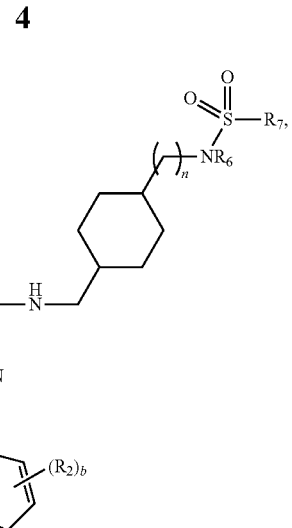

wherein n=0 to 5.

In certain embodiments, n=1. In some embodiments, a compound of any of these formulas is provided, wherein the compound comprises one or more chiral centers.

In further embodiments, a compound is provided according to the following structure:

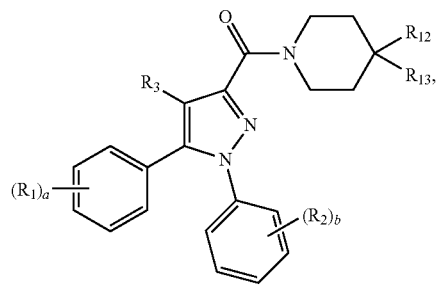

wherein $R_{12}$ and $R_{13}$ are independently selected from H, OH, optionally substituted aryl (e.g., phenyl), $NR_{10}R_{11}$, $NR_{10}COR_{11}$, $NR_{10}SO_2R_{11}$, $NHCONR_{10}R_{10}$, $NR_{10}COOR_{11}$; and $CONR_{10}R_{11}$, wherein at least one of $R_{12}$ and $R_{13}$ is not H.

Certain exemplary compounds that are provided according to the present invention include the following: 4-[5-(4-chlorophenyl)-1-(2,4-dichlorophenyl)-4-methyl-1H-pyrazole-3-amido]pyridin-1-ium-1-olate; 5-[5-(4-chlorophenyl)-1-(2,4-dichlorophenyl)-4-methyl-1H-pyrazole-3-amido]-2-methylpyridin-1-ium-1-olate; 2-[5-(4-chlorophenyl)-1-(2,4-dichlorophenyl)-4-methyl-1H-pyrazole-3-amido]-5-methylpyridin-1-ium-1-olate;
5-(4-chlorophenyl)-1-(2,4-dichlorophenyl)-N-(7-methanesulfonamidoheptyl)-4-methyl-1H-pyrazole-3-carboxamide; 5-(4-chlorophenyl)-1-(2,4-dichlorophenyl)-4-methyl-N-[(1r,4r)-4-methanesulfonamido-cyclohexyl]-1H-pyrazole-3-carboxamide; 5-(4-chlorophenyl)-1-(2,4-dichlorophenyl)-N-{[4-(methanesulfonamidomethyl)cyclohexyl]methyl}-4-methyl-1H-pyrazole-3-carboxamide; 5-(4-chlorophenyl)-1-(2,4-dichlorophenyl)-4-methyl-N-{[(1s,4s)-4-(methanesulfonamidomethyl)cyclohexyl]methyl}-1H-pyrazole-3-carboxamide; 5-(4-chlorophenyl)-1-(2,4-dichlorophenyl)-N-{3-[(3-methanesulfonamidopropyl)(methyl)amino]propyl}-4-methyl-1H-pyrazole-3-carboxamide; 5-(4-chlorophenyl)-1-(2,4-dichlorophenyl)-N-{[4-(methanesulfonamidomethyl)phenyl]methyl}-4- methyl-1H-pyrazole-3-carboxamide; 5-(4-chlorophenyl)-1-(2,4-dichlorophenyl)-N-{[3-(methanesulfonamidomethyl)phenyl]methyl}-4-methyl-1H-pyrazole-3-carboxamide; 5-(4-chlorophenyl)-1-(2,4-dichlorophenyl)-4-methyl-N-[7-(sulfamoylamino)heptyl]-1H-pyrazole-3-carboxamide; 5-(4-chlorophenyl)-1-(2,4-dichlorophenyl)-4-methyl-N-[(1r,4r)-4-(sulfamoylamino)cyclohexyl]-1H-pyrazole-3-carboxamide; 5-(4-chlorophenyl)-1-(2,4-dichlorophenyl)-4-methyl-N-{[3-(sulfamoylamino)methyl]cyclohexyl}methyl)-1H-pyrazole-3-carboxamide; 5-(4-chlorophenyl)-1-(2,4-dichlorophenyl)-4-methyl-N-{[(1s,4s)-4-[(sulfamoylamino)methyl]cyclohexyl]methyl}-1H-pyrazole-3-carboxamide; 5-(4-chlorophenyl)-1-(2,4-dichlorophenyl)-4-methyl-N-({4-[(sulfamoylamino)methyl]phenyl}methyl)-1H-pyrazole-3-carboxamide; 5-(4-chlorophenyl)-1-(2,4-dichlorophenyl)-4-methyl-N-({3-[(sulfamoylamino)methyl]phenyl}methyl)-1H-pyrazole-3-carboxamide; 1-{[5-(4-chlorophenyl)-1-(2,4-dichlorophenyl)-4-methyl-1H-pyrazol-3-yl]carbonyl}-4-phenylpiperidine-4-carboxamide; 1-{[5-(4-chlorophenyl)-1-(2,4-dichlorophenyl)-4-methyl-1H-pyrazol-3-yl]carbonyl}-4-(ethylamino)piperidine-4-carboxamide; 1-{[1-(2,4-dichlorophenyl)-5-[4-(dimethylamino)phenyl]-4-methyl-1H-pyrazol-3-yl]carbonyl}-4-phenylpiperidin-4-ol; 1-{[5-(4-bromophenyl)-1-(2,4-dichlorophenyl)-4-methyl-1H-pyrazol-3-yl]carbonyl}-4-phenylpiperidine-4-carboxamide; 1-{[5-(4-bromophenyl)-1-(2,4-dichlorophenyl)-4-methyl-1H-pyrazol-3-yl]carbonyl}-4-hydroxy-4-phenylpiperidine; tert-Butyl N-(1-{[5-(4-chlorophenyl)-1-(2,4-dichlorophenyl)-4-methyl-1H-pyrazol-3-yl]carbonyl}-4-phenylpiperidin-4-yl)carbamate; 1-{[5-(4-chlorophenyl)-1-(2,4-dichlorophenyl)-4-methyl-1H-pyrazol-3-yl]carbonyl}-4-phenylpiperidin-4-amine; 1-{[5-(4-chlorophenyl)-1-(2,4-dichlorophenyl)-4-methyl-1H-pyrazol-3-yl]carbonyl}-4-hydroxy-4-phenylpiperidine; N-(1-{[5-(4-chlorophenyl)-1-(2,4-dichlorophenyl)-4-methyl-1H-pyrazol-3-yl]carbonyl}-4-phenylpiperidin-4-yl)acetamide; N-(1-{[5-(4-chlorophenyl)-1-(2,4-dichlorophenyl)-4-methyl-1H-pyrazol-3-yl]carbonyl}-4-phenylpiperidin-4-yl)methanesulfonamide; 4-[1-(2,4-dichlorophenyl)-3-[(4-hydroxy-4-phenylpiperidin-1-yl)carbonyl]-4-methyl-1H-pyrazol-5-yl]benzonitrile; 3-tert-butyl-1-(1-{[5-(4-chlorophenyl)-1-(2,4-dichlorophenyl)-4-methyl-1H-pyrazol-3-yl]carbonyl}-4-phenylpiperidin-4-yl)urea; tert-butyl 4-[5-(4-chlorophenyl)-1-(2,4-dichlorophenyl)-4-methyl-1H-pyrazole-3-amido]piperidine-1-carboxylate; 5-(4-chlorophenyl)-1-(2,4-dichlorophenyl)-4-methyl-N-(piperidin-4-yl)-1H-pyrazole-3-carboxamide; N-(1-acetylpiperidin-4-yl)-5-(4-chlorophenyl)-1-(2,4-dichlorophenyl)-4-methyl-1H-pyrazole-3-carboxamide; 5-(4-chlorophenyl)-1-(2,4-dichlorophenyl)-N-(1-methanesulfonylpiperidin-4-yl)-4-methyl-1H-pyrazole-3-carboxamide; 1-N-tert-butyl-4-C-5-(4-chlorophenyl)-1-(2,4-dichlorophenyl)-4-methyl-1H-pyrazole-3-piperidine-1,4-diamido; propan-2-yl 4-[5-(4-chlorophenyl)-1-(2,4-dichlorophenyl)-4-methyl-1H-pyrazole-3-amido]piperidine-1-carboxylate; butyl 4-[5-(4-chlorophenyl)-1-(2,4-dichlorophenyl)-4-methyl-1H-pyrazole-3-amido]piperidine-1-carboxylate; methyl 4-[5-(4-chlorophenyl)-1-(2,4-dichlorophenyl)-4-methyl-1H-pyrazole-3-amido]piperidine-1-carboxylate; ethyl 4-[5-(4-chlorophenyl)-1-(2,4-dichlorophenyl)-4-methyl-1H-pyrazole-3-amido]piperidine-1-carboxylate; tert-butyl N-(1-[5-(4-chlorophenyl)-1-(2,4-dichlorophenyl)-4-methyl-1H-pyrazol-3-yl]carbonyl 1 piperidin-4-yl)carbamate; 1-{[5-(4-chlorophenyl)-1-(2,4-dichlorophenyl)-4-methyl-1H-pyrazol-3-yl]carbonyl}piperidin-4-amine; 1-(1-{[5-(4-chlorophenyl)-1-(2,4-dichlorophenyl)-4-methyl-1H-pyrazol-3-yl]carbonyl}piperidin-4-yl)-3-(propan-2-yl)urea; 1-(1-{[5-(4-chlorophenyl)-1-(2,4-dichlorophenyl)-4-methyl-1H-pyrazol-3-yl]carbonyl}piperidin-4-yl)-3-propylurea; 3-butyl-1-(1-{[5-(4-chlorophenyl)-1-(2,4-dichlorophenyl)-4-methyl-1H-pyrazol-3-yl]carbonyl}piperidin-4-yl)urea; N-(1-{[5-(4-chlorophenyl)-1-(2,4-dichlorophenyl)-4-methyl-1H-pyrazol-3-yl]carbonyl}piperidin-4-yl)methanesulfonamide; 1-(1-{[5-(4-chlorophenyl)-1-(2,4-dichlorophenyl)-4-methyl-1H-pyrazol-3-yl]carbonyl}-4-phenylpiperidin-4-yl)-3-hexylurea; 1-(1-{[5-(4-chlorophenyl)-1-(2,4-dichlorophenyl)-4-methyl-1H-pyrazol-3-yl]carbonyl}-4-phenylpiperidin-4-yl)-3-(propan-2-yl)urea; 1-(1-{[5-(4-chlorophenyl)-1-(2,4-dichlorophenyl)-4-methyl-1H-pyrazol-3-yl]carbonyl}-4-phenylpiperidin-4-yl)-3-ethylurea; 1-(1-{[5-(4-chlorophenyl)-1-(2,4-dichlorophenyl)-4-methyl-1H-pyrazol-3-yl]carbonyl}-4-phenylpiperidin-4-yl)-3-propylurea; 3-(1-{[5-(4-chlorophenyl)-1-(2,4-dichlorophenyl)-4-methyl-1H-pyrazol-3-yl]carbonyl}-4-phenylpiperidin-4-yl)-1-cyclohexylurea; 3-butyl-1-(1-{[5-(4-chlorophenyl)-1-(2,4-dichlorophenyl)-4-methyl-1H-pyrazol-3-yl]carbonyl}-4-phenylpiperidin-4-yl)urea; 4-C-5-(4-chlorophenyl)-1-(2,4-dichlorophenyl)-4-methyl-1H-pyrazole-3-piperidine-1,4-diamido; 4-C-5-(4-chlorophenyl)-1-(2,4-dichlorophenyl)-4-methyl-1H-pyrazole-3-1-N-ethylpiperidine-1,4-diamido; 4-C-5-(4-chlorophenyl)-1-(2,4-dichlorophenyl)-4-methyl-1H-pyrazole-3-1-N-(propan-2-yl)piperidine-1,4-diamido; 4-C-5-(4-chlorophenyl)-1-(2,4-dichlorophenyl)-4-methyl-1H-pyrazole-3-1-N-propylpiperidine-1,4-diamido; 1-N-butyl-4-C-5-(4-chlorophenyl)-1-(2,4-dichlorophenyl)-4-methyl-1H-pyrazole-3-piperidine-1,4-diamido; ethyl 4-[5-(4-chlorophenyl)-1-(2,4-dichlorophenyl)-4-methyl-1H-pyrazole-3-amido]piperidine-1-carboxylate, and N-(tert-butyl)-1-(5-(4-chlorophenyl)-1-(2,4-dichlorophenyl)-methyl-1H-pyrazole-3-carbonyl)-4-phenylpiperidine-4-carboxamide; or a pharmaceutically acceptable ester, amide, salt, solvate, prodrug, or isomer thereof.

In some embodiments, a compound according to one of the following structures is provided:

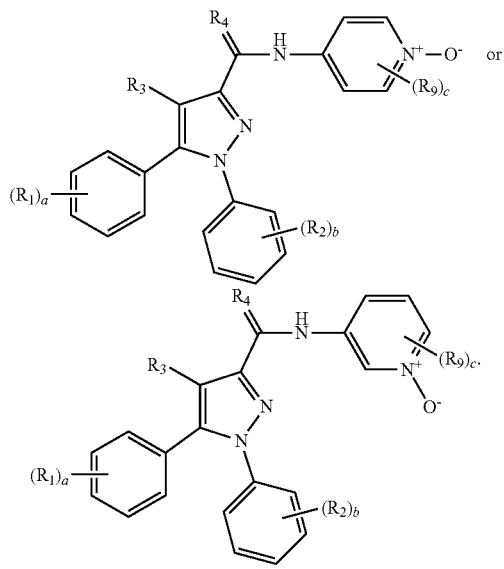

In another aspect of the invention is provided a method for treating or delaying the progression of disorders that are alleviated by antagonizing the CB1 receptor, the method comprising administering a compound as disclosed herein. The disorder can be any disorder that is responsive to antagonism of the CB1 receptor. For example, in certain embodiments, the disorder is selected from the group consisting of obesity, liver diseases, diabetes, pain, inflammation, and dyslipidemia.

In another aspect, a pharmaceutical composition is provided, comprising any of the compounds disclosed herein and one or more pharmaceutically acceptable carriers.

DETAILED DESCRIPTION OF THE INVENTION

The present invention now will be described more fully hereinafter. However, the invention may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

The present invention provides compounds that may function as antagonists at the CB1 receptor, as well as methods of preparation and pharmaceutical compositions thereof. It also provides methods for using such compounds to treat a variety of disorders that may be responsive to the antagonism of CB1 receptors. In particular, the compositions and methods can be used in the treatment of obesity. Treatment can comprise the use of a compound of the present invention as a single active agent. In other embodiments, treatment can comprise the use of a compound of the present invention in combination with one or more further active agents. The specific pharmaceutical composition (or compositions) used in the invention, and the methods of treatment provided by the invention, are further described below.

DEFINITIONS

The term "alkyl" as used herein means saturated straight, branched, or cyclic hydrocarbon groups (i.e., cycloalkyl groups). In particular embodiments, alkyl refers to groups comprising 1 to 10 carbon atoms ("C1-10 alkyl"). In further embodiments, alkyl refers to groups comprising 1 to 8 carbon atoms ("C1-8 alkyl"), 1 to 6 carbon atoms ("C1-6 alkyl"), or 1 to 4 carbon atoms ("C1-4 alkyl"). In other embodiments, alkyl refers to groups comprising 3-10 carbon atoms ("C3-10 alkyl"), 3-8 carbon atoms ("C3-8 alkyl"), or 3-6 carbon atoms ("C3-6 alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The term "heteroalkyl" as used herein means an alkyl group, having at least one atom within the chain which is not carbon. Preferred heteroatoms include sulfur, oxygen, and nitrogen.

"Optionally substituted" in reference to a substituent group refers to substituent groups optionally substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "alkenyl" as used herein means alkyl moieties wherein at least one saturated CC bond is replaced by a double bond. In particular embodiments, alkenyl refers to groups comprising 2 to 10 carbon atoms ("C2-10 alkenyl"). In further embodiments, alkenyl refers to groups comprising 2 to 8 carbon atoms ("C2-8 alkenyl"), 2 to 6 carbon atoms ("C2-6 alkenyl"), or 2 to 4 carbon atoms ("C2-4 alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated CC bond is replaced by a triple bond. In particular embodiments, alkynyl refers to groups comprising 2 to 10 carbon atoms ("C2-10 alkynyl"). In further embodiments, alkynyl refers to groups comprising 2 to 8 carbon atoms ("C2-8 alkynyl"), 2 to 6 carbon atoms ("C2-6 alkynyl"), or 2 to 4 carbon atoms ("C2-4 alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy").

The term "halo" or "halogen" as used herein means fluorine, chlorine, bromine, or iodine.

The term "alkylthio" as used herein means a thio group with one or more alkyl substituents, where alkyl is defined as above.

The terms "aralkyl" and "arylalkyl" as used herein mean an aryl group as defined above linked to the molecule through an alkyl group as defined above.

The terms "alkaryl" and "alkylaryl" as used herein means an alkyl group as defined above linked to the molecule through an aryl group as defined below.

The term "alkylarylalkyl" as used herein means an alkyl group as defined above linked to the molecule through an arylalkyl group as defined above.

The term "amino" as used herein means a moiety represented by the structure $NR_2$, and includes primary amines, and secondary and tertiary amines substituted by alkyl or aryl (i.e., alkylamino or arylamino, respectively). Thus, $R_2$ may represent two hydrogen atoms, two alkyl moieties, two aryl moieties, one aryl moiety and one alkyl moiety, one hydrogen atom and one alkyl moiety, or one hydrogen atom and one aryl moiety.

The tem "cycloalkyl" means a non-aromatic, monocyclic or polycyclic ring comprising carbon and hydrogen atoms.

The term "aryl" as used herein means a stable monocyclic, bicyclic, or tricyclic carbon ring of up to 8 members in each ring, wherein at least one ring is aromatic as defined by the Hückel 4n+2 rule. Exemplary aryl groups according to the invention include phenyl, naphthyl, tetrahydronaphthyl, and biphenyl.

The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the invention.

The term "active metabolite" as used herein means a physiologically active compound which results from the metabolism of a compound of the invention, or a prodrug thereof, when such compound or prodrug is administered to a mammal.

The terms "therapeutically effective amount" or "therapeutically effective dose" as used herein are interchangeable and mean a concentration of a compound according to the invention, or a biologically active variant thereof, sufficient to elicit the desired therapeutic effect according to the methods of treatment described herein.

The term "pharmaceutically acceptable carrier" as used herein means a carrier that is conventionally used in the art to facilitate the storage, administration, and/or the healing effect of a biologically active agent.

The term "intermittent administration" as used herein means administration of a therapeutically effective dose of a composition according to the invention, followed by a time period of discontinuance, which is then followed by another administration of a therapeutically effective dose, and so forth.

Active Agents

The present invention provides compounds, methods of preparation of the compounds, pharmaceutical compositions, and methods of treatment of various conditions using such compounds and pharmaceutical compositions.

In some embodiments, compounds according to the following structure are provided:

Formula 1

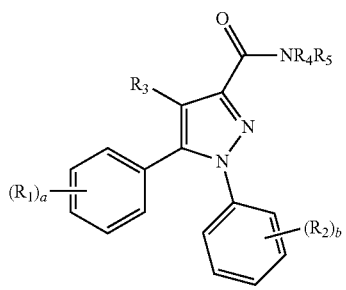

wherein:

each $R_1$ and $R_2$ is a substituent independently selected from the group consisting of Cl, F, Br, OH, optionally substituted C1-10 alkyl, optionally substituted C1-10 alkoxy, optionally substituted C2-4 alkenyl, optionally substituted $C_{2-4}$ alkynyl, $NR_{10}R_{11}$, $NHCOR_{10}$, $NHCO_2R_{10}$, $CH_2OR_{10}$, $CONR_{10}R_{11}$, $CO_2R_{10}$, CN, $CF_3$, $NO_2$, $N_3$, C1-3 alkylthio, $R_{10}SO$, $R_{10}SO_2$, $CF_3S$, and $CF_3SO_2$;

$R_3$ is H or C1-3 alkyl;

$R_4$ is H or C1-10 alkyl;

$R_5$ is selected from:

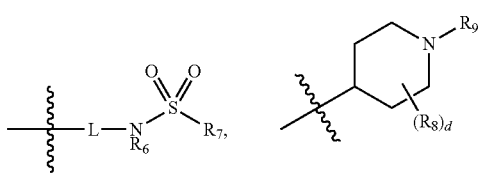

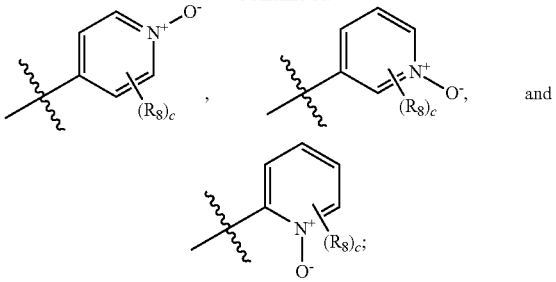

or $R_4$ and $R_5$ taken together form a piperidine ring with the N to which they are attached, which is substituted at the 4 position with one or two substituents selected from the group consisting of OH, optionally substituted aryl (e.g., phenyl), $NR_{10}R_{11}$, $NR_{10}SO_2R_{11}$, $NHCONR_{10}R_{11}$, $NR_{10}OR_{11}$; and $CONR_{10}R_{11}$, $R_6$ is H or C1-10 alkyl;

$R_7$ is C1-10 alkyl, $NR_{10}R_{11}$, or $NR_{10}COR_{11}$;

$R_8$ is C1-10 alkyl;

$R_9$ is H, C1-10 alkyl, acyl, amido, acylamido, $SO_2R_{10}$, $CONR_{10}R_{11}$, or $COOR_{10}$;

$R_{10}$ and $R_{11}$ are independently selected from H and C1-10 alkyl;

L is a linker, selected from:
optionally substituted C1-15 alkyl and C1-15 heteroalkyl, wherein the alkyl or heteroalkyl may comprise one or more cycloalkyl or cycloheteroalkyl rings;
optionally substituted alkylaryl;
optionally substituted arylalkyl; and
optionally substituted alkylarylalkyl;

a and b are each independently integers from 0 to 5; and c is an integer from 0 to 4;

d is an integer from 0 to 8;

or a pharmaceutically acceptable ester, amide, salt, solvate, prodrug, or isomer thereof.

In some preferred embodiments, the phenyl rings of Formula 1 comprise one or more substituents. For example, in some embodiments, a is 1 and the substituent $R_1$ is located at the para position. In some embodiments, b is 2 and the $R_2$ substituents are located at the ortho and para positions. The $R_1$ and $R_2$ substituents may be the same or different. In certain embodiments, both $R_1$ and $R_2$ are halo substituents (e.g., Cl).

In some preferred embodiments, $R_3$ is methyl. In some embodiments, $R_4$ is H. In certain embodiments, $R_6$ is H. In certain embodiments, $R_7$ is selected from H, $CH_3$, and $NH_2$.

In certain embodiments, L comprises one or more cycloalkyl groups, for example, a cyclohexyl group. In some embodiments, L comprises alkyl-cycloalkyl-alkyl, wherein the cycloalkyl group is bound to $NR_4$ through a C1-C5 alkyl chain and is bound to $NR_6$ through a C1-C5 alkyl chain, e.g., alkyl-cyclohexyl-alkyl. For example, L can be $CH_2$—$C_6H_{10}$—$CH_2$. In certain embodiments, L can comprise an unsubstituted straight chain alkyl group (e.g., a C7 alkyl). In some embodiments, L comprises one or more aryl groups, for example, phenyl. In some embodiments, L comprises alkyl-aryl-alkyl, e.g., alkyl-phenyl-alkyl. In certain embodiments, longer L groups are preferred. For example, in some embodiments, the number of carbon atoms in sequence between the nitrogen to which $R_4$ is attached and the nitrogen to which $R_6$ is attached is above a certain value, for example, greater than 4 carbon atoms, greater than 5 carbon atoms, or greater than 6 carbon atoms.

In Formula 1 and other subgenus structures within this application, certain substituents are noted to comprise "C1-10 alkyl" groups. Each reference herein to "C1-10 alkyl" groups is intended to include, for example, C1-5 alkyl groups and C1-3 alkyl groups. Therefore, it should be understood that structures comprising a C1-5 alkyl and/or a C1-3 alkyl in place of a C1-10 alkyl in any of the formulas provided herein are encompassed by the present invention. Similarly, "C1-15 alkyl" groups in any of the formulas provided herein are intended to include smaller ranges such as C1-12, C1-10, C1-8, C1-5, and C1-3 alkyl groups.

Certain compounds according to Formula 1 are compounds with relatively high topological polar surface areas ("TPSA"s). TPSA has been shown to correlate to passive transport through membranes. In certain embodiments, it is desirable to provide compounds with minimal blood-brain barrier penetration. Such compounds may target peripheral receptors and thus reduce potential central nervous system-related side effects. Generally, higher TPSA values correspond to lower penetration into the CNS and may thus be desirable.

A TPSA can be calculated for any given compound to predict that compound's ability to penetrate the blood-brain barrier. Various methods can be used for such calculations and predictions, such as computational models. For example, methods for calculating molecular polar surface area as a sum of fragment based contributions are described in Ertl et al., *J. Med. Chem.* 43: 3714-3417 (2000), which is incorporated herein by reference. In certain embodiments, TPSA values for compounds are calculated using commercially available software from Advanced Chemistry Development (ACD 10, ACD/ChemSketch). In some preferred embodiments, compounds of Formula 1 are provided, wherein the TPSAs of such compounds are greater than that of rimonabant (i.e., greater than about 50). For example, in certain embodiments, the TPSAs of compounds according to the present invention are greater than about 55, greater than about 60, greater than about 65, greater than about 70, or greater than about 75. Certain compounds may exhibit TPSAs of greater than about 80, greater than about 90, or greater than about 100.

Accordingly, in certain embodiments of the present invention, compounds are provided which exhibit relatively low penetration through the blood-brain barrier. For example, compounds may preferably exhibit lower penetration through the blood-brain barrier than rimonabant. Penetration of compounds can be measured by any means, including, but not limited to: in vivo methods such as intravenous injection/brain sampling, brain uptake index, brain perfusion, quantitative autoradiography, external registration (MRI, SPECT, PET), microdialysis, or CSF sampling; and in vitro methods such as binding, uptake, and efflux measurements on fresh isolated brain microvessels and endothelial cell cultures. Reviews of various methods for prediction and measurement of blood-brain barrier penetration can be found in Bickel, *NeuroRx®* 2:15-26 (2005) and Liu, *Drug Metabolism and Disposition* 32(1): 132-139 (2004), which are both incorporated herein by reference.

Certain compounds according to Formula 1 are sulfamide or sulfonamide compounds, as shown below in Formula 1A, as well as pharmaceutically acceptable esters, amides, salts, solvates, prodrugs, or isomers thereof. In some embodiments, compounds of Formula 1A have TPSAs higher than about 50. For example, certain specific sulfonamides and sulfamides according to Formula 1A have TPSA values greater than about 60 or greater than about 75 (e.g., between about 75 and about 150).

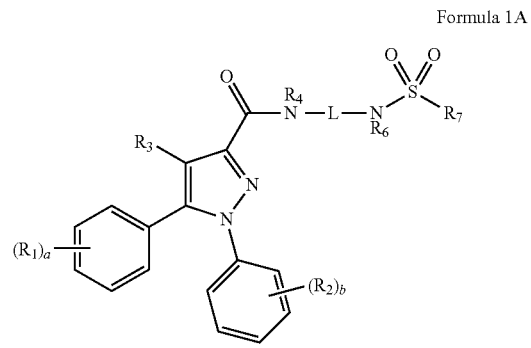

Formula 1A

In some embodiments, compounds of FIG. 1B are provided, as well as pharmaceutically acceptable esters, amides, salts, solvates, prodrugs, or isomers thereof, wherein L comprises a cyclohexyl subunit within a linear alkyl linker (n is from 0 to 5). In certain preferred embodiments, n=1. In certain preferred embodiments, $R_7$ is selected from H, $CH_3$, and $NH_2$.

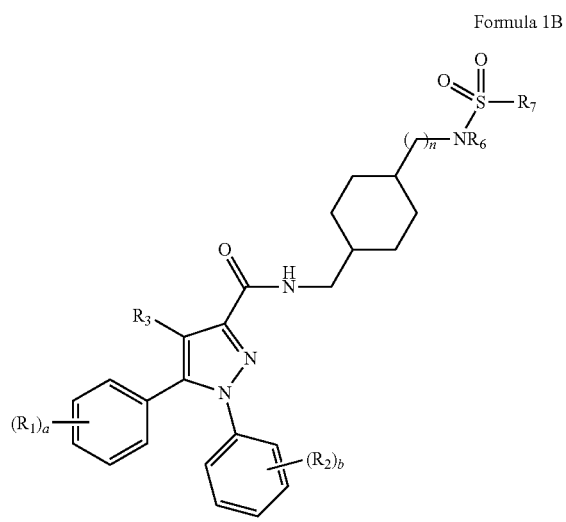

Formula 1B

In certain embodiments, compounds of FIG. 1C are provided, as well as pharmaceutically acceptable esters, amides, salts, solvates, prodrugs, or isomers thereof, wherein $R_{12}$ and $R_{13}$ are independently selected from H, OH, optionally substituted aryl (e.g., phenyl), $NR_{10}R_{11}$, $NR_{10}COR_{11}$, $NR_{10}SO_2R_{11}$, $NHCONR_{10}R_{11}$, $NR_{10}COOR_{11}$, and $CONR_{10}R_{11}$, and wherein at least one of $R_{12}$ and $R_{13}$ is a substituent other than H.

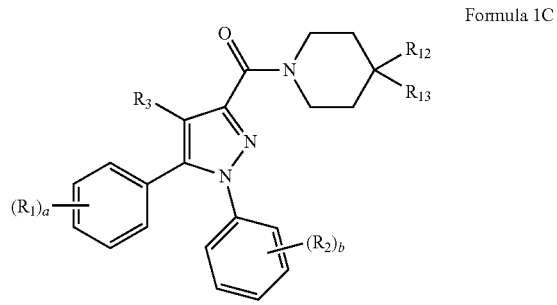

Formula 1C

Certain other compounds according to Formula 1 are charged compounds. These compounds may, in certain embodiments, be beneficial in avoiding the CNS-related side effects, as charged compounds typically do not cross the blood brain barrier unless transported by specific transporters. Charged compounds according to the present invention comprise pyridine N-oxides according to Formula 1D or 1E or pharmaceutically acceptable esters, amides, salts, solvates, prodrugs, or isomers thereof

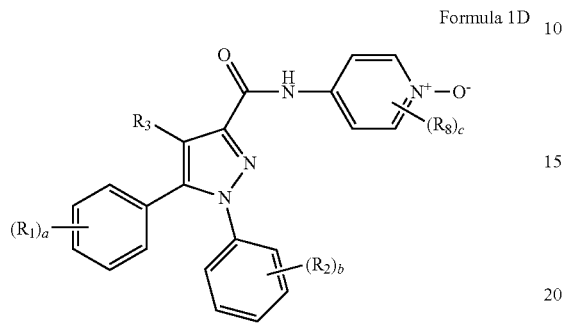

Formula 1D

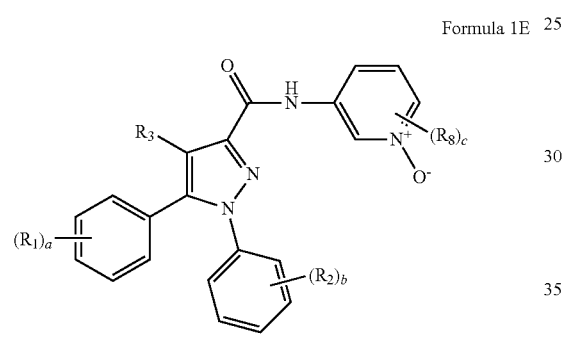

Formula 1E

The compounds disclosed herein as active agents may contain chiral centers, which may be either of the (R) or (S) configuration, or may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

In some embodiments, the compounds of Formula 1 are racemic. In some embodiments, compounds with one or more chiral centers are provided. While racemic mixtures of compounds of the invention can be active, selective, and bioavailable, isolated isomers may be of interest as well. The compounds of the present invention optionally may be provided in a composition that is enantiomerically enriched, such as a mixture of enantiomers in which one enantiomer is present in excess, in particular to the extent of 95% or more, or 98% or more, including 100%.

Although racemic mixtures and all possible stereoisomers are encompassed by this disclosure, in some preferred embodiments, compounds of the following formula are provided:

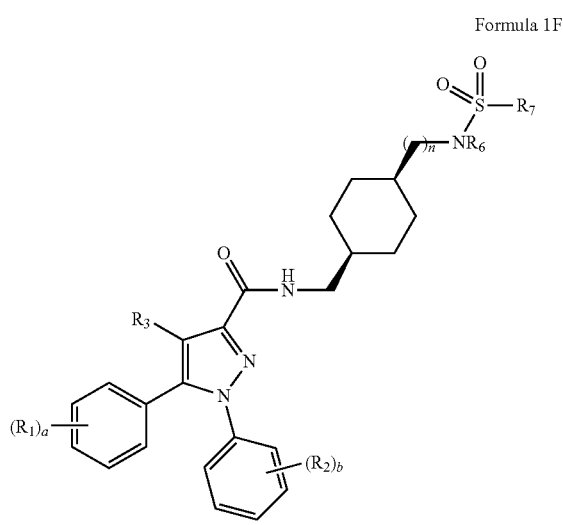

Formula 1F or a pharmaceutically acceptable ester, amide, salt, solvate, prodrug, or isomer thereof.

Various methods are known in the art for preparing optically active forms and determining activity. Such methods include standard tests described herein other similar tests which are will known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The terms (R) and (S) as used herein mean that the composition contains a greater proportion of the named isomer of the compound in relation to other isomers. In a preferred embodiment these terms indicate that the composition contains at least 90% by weight of the named isomer and 10% by weight or less of the one or more other isomers; or more preferably about 95% by weight of the named isomer and 5% or less of the one or more other isomers. These percentages are based on the total amount of the compound of the present invention present in the composition.

The compounds of the present invention may be utilized per se or in the form of a pharmaceutically acceptable ester, amide, salt, solvate, prodrug, or isomer. For example, the compound may be provided as a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature. Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1, 4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound useful according to the present invention may be prepared in a similar manner using a pharmaceutically acceptable base, such as sodium hydroxide, potassium hydroxide, ammonium hydroxide, calcium hydroxide, triethylamine, or the like.

Esters of the active agent compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters, urease, sulfonamides, and amides of compounds of the invention can be made by reaction with a carbonylating agent (e.g., ethyl formate, acetic anhydride, methoxyacetyl chloride, benzoyl chloride, methyl isocyanate, ethyl chloroformate) or methanesulfonyl chloride and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the methods of the invention may exist in different forms. For example, the compounds may exist in stable and metastable crystalline forms and isotropic and amorphous forms, all of which are intended to be within the scope of the present invention.

If a compound useful as an active agent according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound described herein as an active agent is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

The present invention further includes prodrugs and active metabolites of the active agent compounds described herein. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

A number of prodrug ligands are known. In general, alkylation, acylation, or other lipophilic modification of one or more heteroatoms of the compound, such as a free amine or carboxylic acid residue, reduces polarity and allows passage into cells. Examples of substituent groups that can replace one or more hydrogen atoms on the compounds of the present invention include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free moiety, e.g., amine and/or carboxylic acid moiety. Any of these can be used in combination with the disclosed active agents to achieve a desired effect.

Particularly preferred compounds of the present invention include the following:

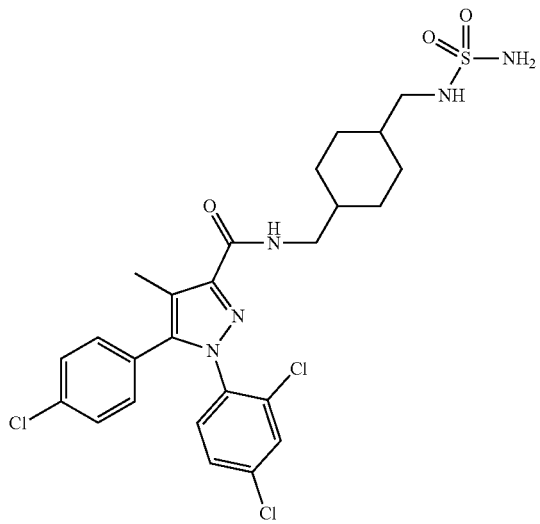

5-(4-chlorophenyl)-1-(2,4-dichlorophenyl)-4-methyl-N-((4-((sulfamoylamino)methyl)cyclohexyl)methyl)-1H-pyrazole-3-carboxamide

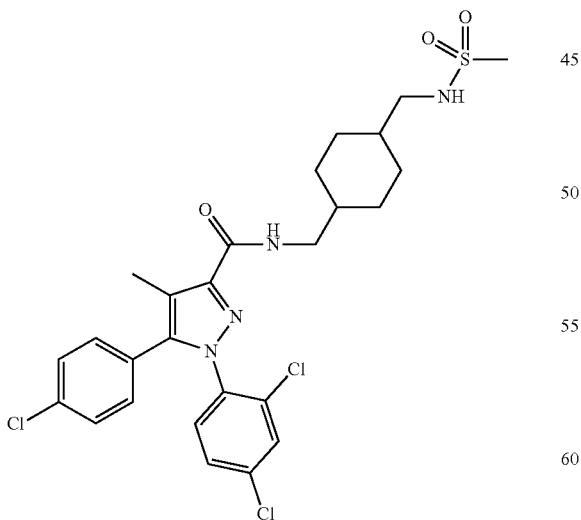

5-(4-chlorophenyl)-1-(2,4-dichlorophenyl)-4-methyl-N-((4-(methylsulfonamidomethyl)cyclohexyl)methyl)-1H-pyrazole-3-carboxamide

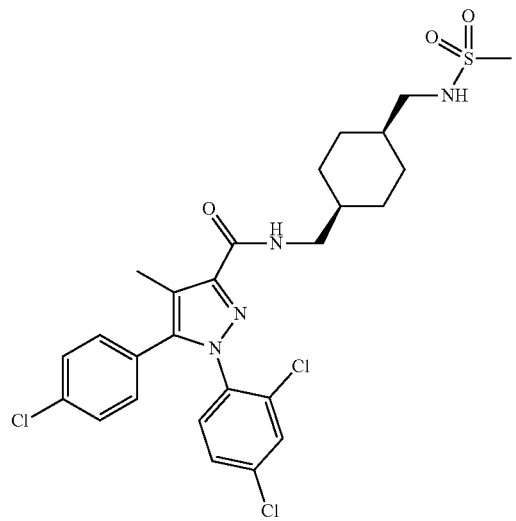

5-(4-chlorophenyl)-1-(2,4-dichlorophenyl)-4-methyl-N-(((1s,4s)-4-(methylsulfonamidomethyl)cyclohexyl)methyl)-1H-pyrazole-3-carboxamide

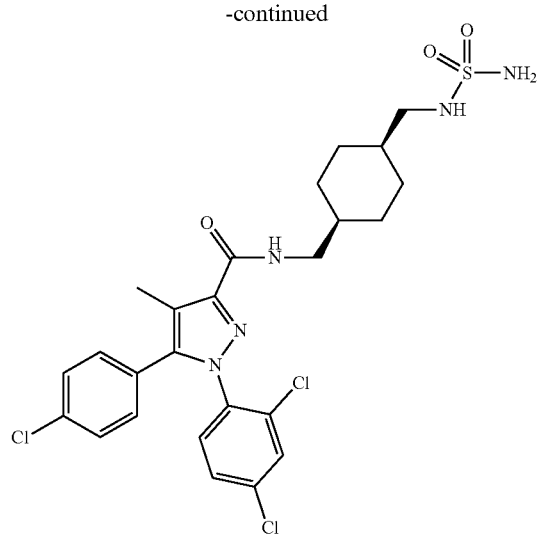

5-(4-chlorophenyl)-1-(2,4-dichlorophenyl)-4-methyl-N-(((1s,4s)-4-((sulfamoylamino)methyl)cyclohexyl)methyl)-1H-pyrazole-3-carboxamide The compounds of the present invention may function as antagonists at the CB1 receptor, but preferably do not cross the blood-brain barrier. Thus, in certain embodiments, the compounds can be described as peripherally restricted CB1 antagonists. Charged compounds (e.g., the N-oxides disclosed herein) typically do not cross the blood-brain barrier unless transported by specific transporters. Compounds with high TPSA (e.g., including, but not limited to, the sulfamides and sulfonamides disclosed herein) typically exhibit lower penetration into the central nervous system (CNS). Certain compounds, such as the sulfamides and sulfonamides of the present invention also have hydrogens available for H bonding, providing the compounds with the ability to interact further with the receptor site, which may lead to improved potency of such compounds. In certain embodiments, the compounds are tailored so as to maximize the TPSA to preclude CNS permeability, but ensuring a reasonable level of oral bioavailability to allow for oral uptake. In preferred embodiments, the compounds of the present invention are selective for the CB1 receptor.

Methods of Preparation

The present invention also encompasses methods of preparing compounds with structures encompassed by Formula 1. One of skill in the art would be able to adapt these methods as required to accommodate various functional groups that may affect the chemistry of the synthesis.

Scheme 1 shows a general synthesis used for some charged compounds of the present invention. Acid A is readily available using a procedure described in Seltzman et al., *J. Label Compd. Radiopharm.* 2002, 45, 59 and Zhang et al., *J. Med. Chem.* 2008, 51, 3526, which are both incorporated herein by reference. The acid is coupled by first making an acid chloride using oxalyl chloride and a catalytic amount of DMF followed by amide formation with the appropriate aminopyridine and triethylamine; or by the use of standard BOP coupling conditions. See, for example, Zhang et al., *J. Med. Chem.* 2010, 53, 7048, which is incorporated herein by reference. Alkyl pyridinium salts can be prepared by reacting B with methyl iodide in dichloromethane or methanol. See, for example, Huang et al., *Tetrahedron Lett.* 2009, 50, 5018, which is incorporated herein by reference. Pyridine N-oxides can be obtained by reacting B with m-CPBA in dichloromethane, as described in Fang et al., *J. Org. Chem.* 2007, 72, 5152, which is incorporated herein by reference.

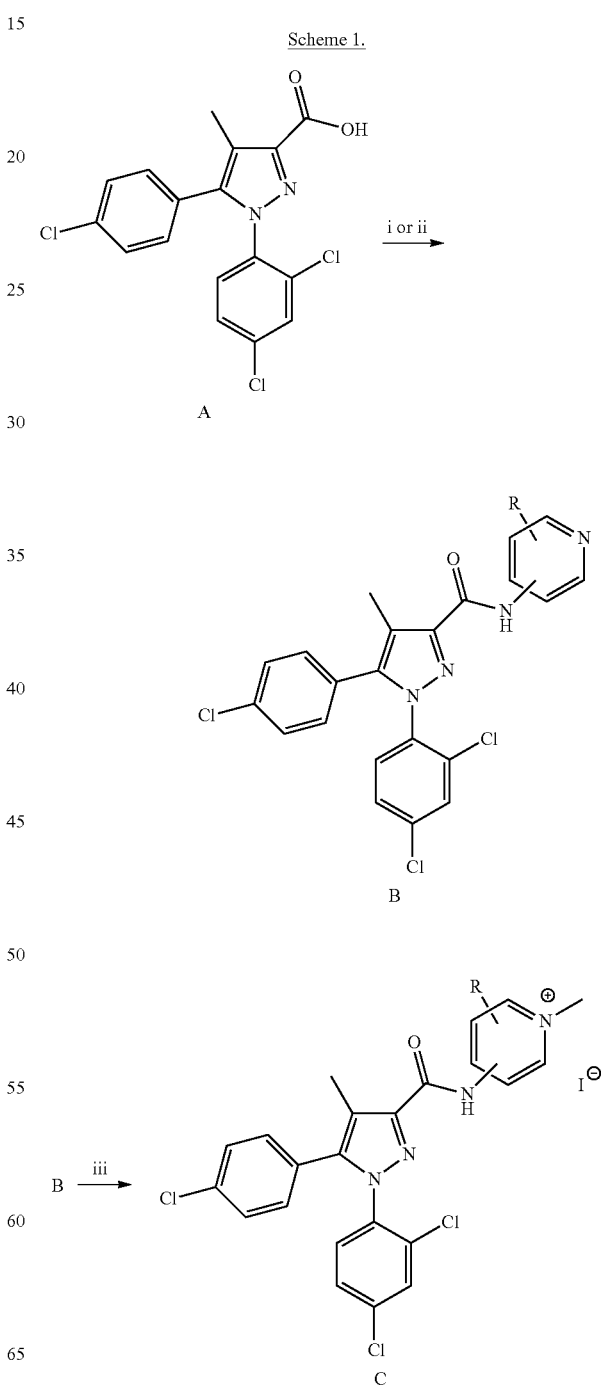

Scheme 1.

-continued

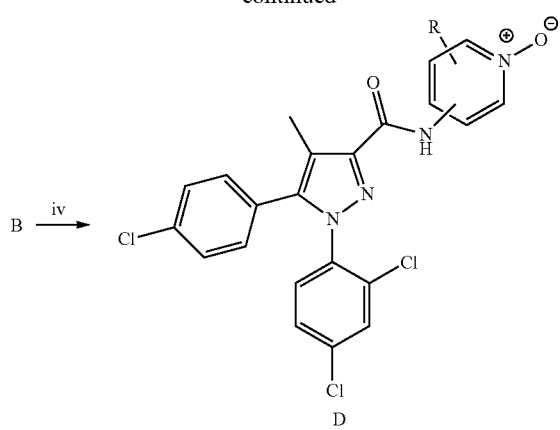

D

Reagents and conditions: (i) (a) oxalyl chloride, CH₂Cl₂, DMF cat., rt, 2 h; (b) aminopyridine, CH₂Cl₂, Et₃N, rt; (ii) aminopyridine, BOP, i-Pr₂EtN, DMF, rt, 16 h; (iii) methyl iodide, CH₂Cl₂ or MeOH, 2-7 d; (iv) m-CPBA, CH₂Cl₂, 16 h.

Certain sulfonamide and sulfamide compounds can be synthesized by the route of Scheme 2. Acid A is coupled to a diamine via a method previously described in Zhang et al., *J. Med. Chem.* 2010, 53, 7048, which is incorporated herein by reference. The diastereomeric ratio of certain compounds can, in certain embodiments, be enriched, such as by column chromatography. These amines can be converted to the corresponding sulfonamide compound with methanesulfonyl chloride and triethylamine in THF. The desired sulfamides can be synthesized by reacting the appropriate amine with sulfamide at an elevated temperature, as has been described in Jones et al., PCT Appl. No. WO2007/138277, which is incorporated herein by reference.

Scheme 2.

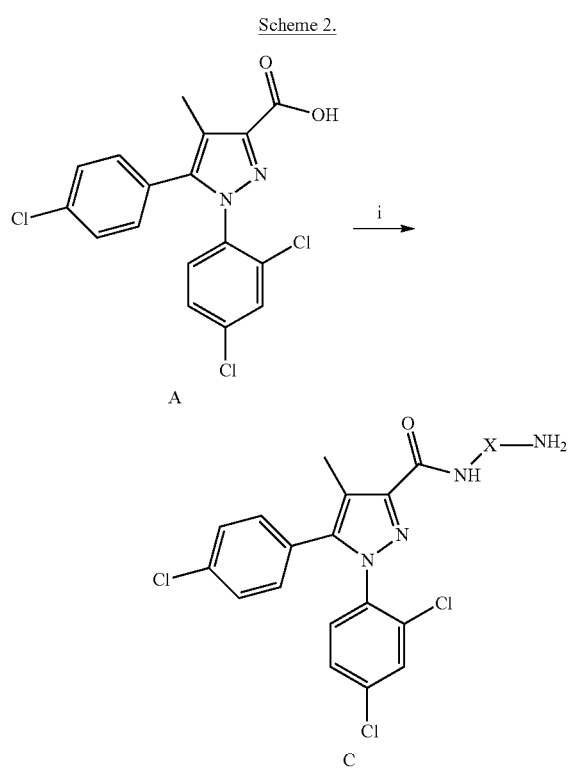

-continued

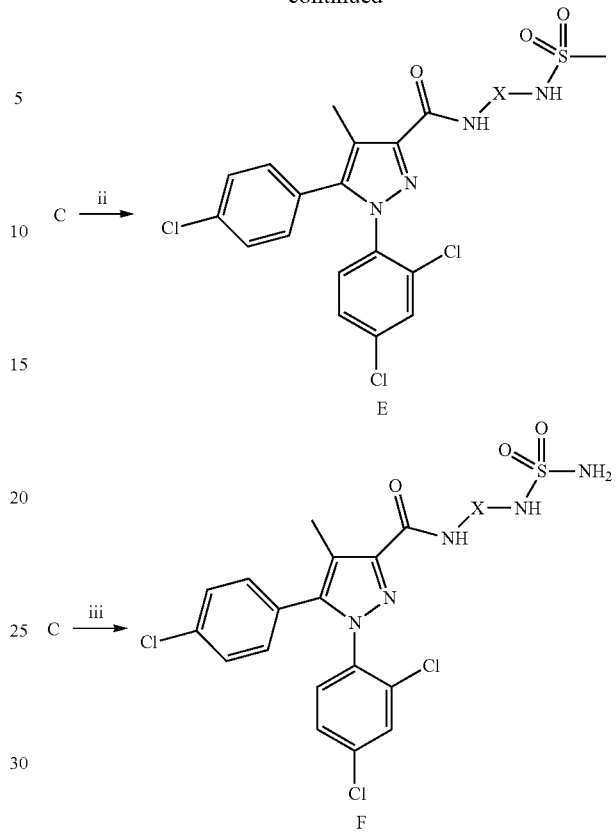

Reagents and conditions: (i) diamine, BOP, THF, rt; (ii) methanesulfonyl chloride, Et₃N, THF, rt, 16 h; (iii) sulfamide, dioxane, 85° C., 16 h. X is used to designate a spacer of any kind.

Compositions

While it is possible for the compounds of the present invention to be administered in the raw chemical form, it is preferred for the compounds to be delivered as a pharmaceutical formulation. Accordingly, there are provided by the present invention pharmaceutical compositions comprising at least one compound capable of functioning as an antagonist of the CB1 receptor. As such, the formulations of the present invention comprise a compound of Formula 1, as described above, or a pharmaceutically acceptable ester, amide, salt, or solvate thereof, together with one or more pharmaceutically acceptable carriers therefore, and optionally, other therapeutic ingredients.

By "pharmaceutically acceptable carrier" is intended a carrier that is conventionally used in the art to facilitate the storage, administration, and/or the healing effect of the agent. The carrier(s) must be pharmaceutically acceptable in the sense of being compatible with the other ingredients of the formulation and not unduly deleterious to the recipient thereof. A carrier may also reduce any undesirable side effects of the agent. Such carriers are known in the art. See, Wang et al. (1980) *J. Parent. Drug Assn.* 34(6):452-462, herein incorporated by reference in its entirety.

Adjuvants or accessory ingredients for use in the formulations of the present invention can include any pharmaceutical ingredient commonly deemed acceptable in the art, such as binders, fillers, lubricants, disintegrants, diluents, surfactants, stabilizers, preservatives, flavoring and coloring agents, and the like. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations).

Exemplary pharmaceutical excipients and/or additives suitable for use in the compositions according to the invention are listed in Remington: The Science & Practice of Pharmacy," $21^{st}$ ed. Lippincott Williams & Wilkins (2006); in the Physician's Desk Reference, $64^{th}$ ed., Thomson PDR (2010); and in Handbook of Pharmaceutical Excipients, $6^{th}$ ed., Eds. Raymond C. Rowe et al., Pharmaceutical Press (2009), which are incorporated herein by reference.

Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluoses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the formulation according to the present invention may be anionic, cationic, amphoteric, or nonionic surface active agents. Stabilizers may be included in the formulations to inhibit or lessen reactions leading to decomposition of the active agent, such as oxidative reactions.

Formulations of the present invention may include short-term, rapid-onset, rapid-offset, controlled release, sustained release, delayed release, and pulsatile release formulations, providing the formulations achieve administration of a compound as described herein. See Remington's Pharmaceutical Sciences ($18^{th}$ ed.; Mack Publishing Company, Eaton, Pa., 1990), herein incorporated by reference in its entirety.

Pharmaceutical formulations according to the present invention are suitable for various modes of delivery, including oral, parenteral (including intravenous, intramuscular, subcutaneous, intradermal, and transdermal), topical (including dermal, buccal, and sublingual), and rectal administration. The most useful and/or beneficial mode of administration can vary, especially depending upon the condition of the recipient and the disorder being treated.

The pharmaceutical formulations may be conveniently made available in a unit dosage form, whereby such formulations may be prepared by any of the methods generally known in the pharmaceutical arts. Generally speaking, such methods of preparation comprise combining (by various methods) an active agent, such as the compounds of Formula II according to the present invention (or a pharmaceutically acceptable ester, amide, salt, or solvate thereof) with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

Pharmaceutical formulations according to the present invention suitable as oral dosage may take various forms, such as tablets, capsules, caplets, and wafers (including rapidly dissolving or effervescing), each containing a predetermined amount of the active agent. The formulations may also be in the form of a powder or granules, a solution or suspension in an aqueous or non-aqueous liquid, and as a liquid emulsion (oil-in-water and water-in-oil). The active agent may also be delivered as a bolus, electuary, or paste. It is generally understood that methods of preparations of the above dosage forms are generally known in the art, and any such method would be suitable for the preparation of the respective dosage forms for use in delivery of the compounds according to the present invention.

A tablet containing a compound according to the present invention may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agent.

Solid dosage forms may be formulated so as to provide a delayed release of the active agent, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agent over a prolonged period of time), and may or may not also be delayed release. Sustained release formulations are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents. Such formulations for patenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compounds according to the present invention may also be administered transdermally, wherein the active agent is incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agent is contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdermal drug delivery may occur through passive diffusion or may be facilitated using electrotransport or iontophoresis.

Formulations for rectal delivery of the compounds of the present invention include rectal suppositories, creams, ointments, and liquids. Suppositories may be presented as the active agent in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

The compounds of Formula 1 above may be formulated in compositions including those suitable for oral, buccal, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing a compound of Formula I into association with a carrier that constitutes one or more accessory ingredients. In general, the compositions are prepared by bringing a compound of the invention into association with a liquid carrier to form a solution or a suspension, or alternatively, bringing a compound of the invention into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter.

The amount of the compound of Formula 1 in the formulation will vary depending on the specific compound selected, dosage form, target patient population, and other considerations, and will be readily determined by one skilled in the art. The amount of the compound of Formula I in the formulation will be that amount necessary to deliver a therapeutically effective amount of the compound to a patient in need thereof to achieve at least one of the therapeutic effects associated with the compounds of the invention. In practice, this will vary widely depending upon the particular compound, its activity, the severity of the condition to be treated, the patient population, the stability of the formulation, and the like. Compositions will generally contain anywhere from about 1% by weight to about 99% by weight of a compound of the invention, typically from about 5% to about 70% by weight, and more typically from about 10% to about 50% by weight, and will also depend upon the relative amounts of excipients/additives contained in the composition.

Combinations

In specific embodiments, active agents used in combination with compounds of the present invention comprise one or more compounds generally recognized as useful for treating the conditions discussed herein. In one embodiment, the use of two or more drugs, which may be of different therapeutic classes, may enhance efficacy and/or reduce adverse effects associated with one or more of the drugs.

For example, in certain embodiments, the present invention relates to the treatment of obesity. Accordingly, in one embodiment, a compound of Formula 1 is combined with one or more known antiobesity drugs for the treatment of obesity. Common therapeutic classes of obesity drugs include those that decrease food intake by either reducing appetite or increasing satiety, those that decrease nutrient absorption, and those that increase energy expenditure. Examples of known antiobesity drugs include: phentermine, which is an appetite suppressant; topiramate, which is an depressant/epilepsy drug that has been shown to interfere with binge eating and may result in decreased weight and decreased blood pressure; Orlistat (Xenical, Alli®), which reduces intestinal fat absorption by inhibiting pancreatic lipase; Sibutramine (Reductil or Meridia), which is an anorectic or appetite suppressant; diethylpropion (diethylcathinone/amfepramone, also sold as Anorex,® Tenuate,® and Tepanil®), which is a stimulant marketed as an appetite suppressant (which functions as a prodrug for ethcathinone); Mazindol (Mazanor, Sanorex), which is a tetracyclic stimulant drug used for short-term treatment of obesity; Rimonabant (Acomplia), which is a compound that is a cannabinoid (CB1) receptor antagonist that acts centrally on the brain to decrease appetite and may also increase energy expenditure; metformin (glucophage) in people with diabetes mellitus type 2; Exenatide (Byetta) and Pramlintide (Symlin), which both delay gastric emptying and promote a feeling of satiety. Other over-the-counter weight loss products including herbal remedies, laxatives, diet pills, diuretic drugs, and/or pyruvate may also be combined with the compounds disclosed herein. The compounds disclosed herein may also be used in combination with non drug-based therapy, including caloric restriction, exercise, and behavioral therapy.

Combinations of compounds of the present invention with other therapeutic agents are also included in the present invention, wherein the condition to be treated is any condition that is responsive to the antagonism of the CB1 receptor.

For example, diabetes may be treated with compounds of the present invention, and thus, in one embodiment, a compound of Formula 1 is combined with one or more known drugs for the treatment of diabetes. In certain embodiments, diabetes is treated with compounds of the present invention in combination with insulin. Diabetes medications generally fall within six classes of drugs that work in different ways to lower blood glucose levels. Specifically, these medications include sulfonylureas, which stimulate the beta cells of the pancrease to release more insulin (e.g., chlorpropamide (Diabinese), glipizide (Glucotrol and Glucotrol XL), glyburide (Micronase, Glynase, and Diabeta, and glimepiride (Amaryl)); meglitinides, which stimulate the beta cells to release insulin (e.g., repaglinide (Prandin) and nateglinide (Starlix)); biguanides, which lower blood glucose levels primarily by reducing the glucose produced by the liver (e.g., metformin (Glucophage)); thiazolidinediones, which help insulin to work better in the muscle and fat, and also reduce glucose production in the liver (e.g., rosiglitazone (Avandia) and pioglitazone (ACTOS)); alpha-glucosidase inhibitors, which help lower blood glucose levels by blocking the breakdown of starches in the intestine and may slow the breakdown of some sugars (e.g., acarbose (Precose) and meglitol (Glyset)); and DPP-4 inhibitors, which prevent the breakdown of GLP-1, which is a naturally occurring compound in the body that reduces blood glucose levels (e.g., sitagliptin (Januvia) and saxagliptin (Onglyza).

Dyslipidemia may also be treated using compounds with the present invention. Thus, in one embodiment, a compound of Formula 1 is combined with one or more known drugs for the treatment of dyslipidemia. Medications for dyslipidemia typically fall into four classes of compounds capable of lowering lipid levels. These classes include statins, which are 3-hydroxy-3-methylglutaryl coenzyme A (HMG-CoA) reductase inhibitors (e.g., rosuvastatin, lovastatin, atorvastatin, pravastatin, fluvastatin, pitavastatin, and simvastatin); fibrates, which reduce triglyceride and very low-density lipoprotein production in the liver (e.g., gemfibrozil, clofibrate, and fenofibrate); niacin (also known as nicotinic acid or Vitamin B3), which lowers total cholesterol and triglycerides and may also increase high-density lipoprotein cholesterol; and bile acid sequestering resins, which bind bile acids in the small intestine and prevent their return to the liver (e.g., cholestipol and cholestyramine).

Various liver diseases may be treated using compounds of the present invention. Accordingly, in one embodiment, a compound of Formula 1 is combined with one or more known drugs for the treatment of various types of liver disease. For example, exemplary medications used to treat fatty liver disease or nonalcoholic steatohepatitis include Actos, Avandia, Xenical, Actigall, Urso, Urso Forte, Orlostat, and Cystadane.

Further, in one embodiment, a compound of Formula 1 is combined with one or more known drugs for the treatment of pain and/or inflammation. Many such drugs are well known, and include, for example, acetaminophen (e.g., Tylenol and aspirin-free Excedrin); nonsteroidal anti-inflammatory drugs (NSAIDS, e.g., aspirin, Motrin, and Aleve); topical corticosteroids (e.g., Cortaid and Cortizone); corticosteroids (e.g., Deltasone, Hydeltrasol, and Solu-Medrol); opiods (e.g., morphine, fentanyl, oxycodone, and codeine); antidepressants (e.g., selective serotonin reuptake inhibitors (SSRIs) such as Celexa, Prozac, Paxil, and Zoloft; tricyclic antidepressants such as Elavil, Norpramin, Sinequan, Tofranil, and Pamelor; and selective serotonin and norepinephrine reuptake inhibitors (SSNRIs) such as Effexor and Cymbalta); and anticonvulsants (e.g., Tegretol, Neurontin, and Lyrica).

The compound of Formula 1 and the one or more other therapeutic agents may be contained within a single composition or alternatively may be administered concurrently or sequentially (consecutively) in any order. For sequential administration, each of the compound of Formula I and the one or more other therapeutic agents can be formulated in its own pharmaceutical composition, each of which is to be administered sequentially, in any order. Alternatively, the compound of Formula 1 and the one or more other therapeutic agents can be formulated together. The compositions may be formulated for oral, systemic, topical, intravenous, intraparenteral, intravaginal, intraocular, transbuccal, transmucosal, or transdermal administration.

Methods of Use

In a further embodiment, the present invention provides a method for treating or delaying the progression of disorders that are alleviated by antagonizing the CB1 receptors in a patient, the method comprising administering a therapeutically effective amount of at least one compound of Formula 1 to the patient.

In particular, the present invention relates to the field of treating obesity in animals, particularly humans and other mammals, and associated effects of these conditions. It also may relate to the treatment of other conditions that may benefit from the antagonism of CB1 receptors, such as liver diseases, dyslipidemia, pain/inflammation, and metabolic disorder. In some embodiments, the compounds show selectivity for CB1 over other cannabinoid receptors.

Obesity has its common meaning, e.g., the medical condition that exists when an individual has accumulated excess body fat, which may lead to a variety of related health problems, and which is characterized by a body mass index (BMI) of 30 kg/m$^2$ or more. Pre-obesity, also known as overweight, refers to the condition wherein an individual's BMI is between 25 kg/m$^2$ and 30 kg/m$^2$.

The method of treatment generally includes administering a therapeutically effective amount of a compound of Formula 1, optionally in a pharmaceutical composition including one or more pharmaceutically acceptable carriers. The therapeutically effective amount is preferably sufficient to antagonize the CB1 receptor. The therapeutically effective amount is further preferably sufficient to cause some relief to the patient in the symptoms of the disorder for which the patient is being treated.

For example, in one embodiment, a method of treating obesity is provided. In such methods, a therapeutically effective amount of a compound of the present invention to treat a patient with pre-obesity or obesity may be that amount capable of antagonizing the CB1 receptor. Such compound may cause the patient to experience decreased appetite and/or may create a sensation of fullness. The method of treating obesity may be used to attain or maintain a patient's weight loss.

In another embodiment, a method of treating liver disease is provided. The liver disease may be, for example, fatty liver disease or nonalcoholic steatohepatitis (e.g., obesity-related steatosis). For example, compounds of the present invention can, in some embodiments, be used to slow the development of fatty liver (alcoholic or non-alcoholic fatty liver) and, in some cases, prevent the progression of fatty liver to more severe forms of liver disease. In some embodiments, compounds of the present invention may function to provide hepatoprotective activity. In some embodiments, the compounds may be capable of modulating lipid levels, reducing cholesterol, free fatty acids, and/or triglycerides.

In some embodiments, a method of treating diabetes is provided. Diabetes can be type 1, type 2, pre-diabetes, gestational diabetes, or latent autoimmune diabetes of adults (LADA). In some cases, the diabetes is associated with a disorder that has caused damage to the pancreas, such as cystic fibrosis, chronic pancreatitis, or haemochromatosis.

In some embodiments, a method of treating metabolic syndrome, a cluster of conditions such as high blood sugar and high triglycerides that can lead to cardiovascular disease, is provided. In certain other embodiments, a method of smoking cessation and/or a method for preventing weight gain in former smokers is provided.

The therapeutically effective dosage amount of any specific formulation will vary somewhat from drug to drug, patient to patient, and will depend upon factors such as the condition of the patient and the route of delivery. When administered conjointly with other pharmaceutically active agents, even less of the compounds of the invention may be therapeutically effective. Furthermore, the therapeutically effective amount may vary depending on the specific condition to be treated.

The compounds of the invention can be administered once or several times a day. The daily dose can be administered either by a single dose in the form of an individual dosage unit or several smaller dosage units or by multiple administration of subdivided dosages at certain intervals. Possible routes of delivery include buccally, subcutaneously, transdermally, intramuscularly, intravenously, orally, or by inhalation. Exemplary daily dosage ranges may be from about 0.1 mg to about 100 mg.

The compounds of the invention may be used with other types of therapy, including those which are non-drug based. Thus, in some embodiments, the methods of the present invention comprise administering to a subject a compound that that is capable of functioning as an antagonist of CB1 receptors in conjunction with one or more other types of non-drug-based therapy.

EXPERIMENTAL SECTION

Example 1

Synthesis

General Procedure for the Oxidation of (pyridinyl)-1H-pyrazole-3-carboxamides to (pyridinium oxide)-1H-pyrazole-3-carboxamides.

To a solution of (pyridin-4-yl)-1H-pyrazole-3-carboxamide in dichloromethane was added to 77% m-CPBA (1.8 eq). The reaction mixture was stirred for 16 h. Dichloromethane and saturated sodium bicarbonate solution was added. The layers were separated and the aqueous layer was extracted twice with dichloromethane. The combined organic layers were dried with magnesium sulfate. The solution was then filtered and concentrated in vacuo. The crude reaction material was then purified by silica gel column chromatography using 0-50% CMA 80/ethyl acetate to yield pure pyridinium oxide.

4-[5-(4-chlorophenyl)-1-(2,4-dichlorophenyl)-4-methyl-1H-pyrazole-3-amido]pyridin-1-ium-1-olate: $^1$H NMR (300 MHz, CHLOROFORM-d) d ppm 2.41 (s, 3H) 7.05-7.12 (m, 2H) 7.24-7.37 (m, 4H) 7.47 (s, 1H) 7.66-7.73 (m, 2H) 8.16 (d, J=7.54 Hz, 2H) 9.07 (s, 1H).

5-[5-(4-chlorophenyl)-1-(2,4-dichlorophenyl)-4-methyl-1H-pyrazole-3-amido]-2-methylpyridin-1-ium-1-olate: $^1$H NMR (300 MHz, CHLOROFORM-d) d ppm 2.38-2.42 (m, 3H) 2.50 (s, 3H) 7.04-7.12 (m, 2H) 7.18-7.24 (m, 1H) 7.26-7.37 (m, 4H) 7.44-7.49 (m, 1H) 7.56-7.62 (m, 1H) 8.73-8.84 (m, 1H) 8.84-8.90 (m, 1H).

2-[5-(4-chlorophenyl)-1-(2,4-dichlorophenyl)-4-methyl-1H-pyrazole-3-amido]-5-methylpyridin-1-ium-1-olate: $^1$H NMR (300 MHz, CHLOROFORM-d) d ppm 2.26-2.34 (m, 3H) 2.36-2.46 (m, 3H) 7.06-7.11 (m, 2H) 7.17 (dd, J=8.59, 1.44 Hz, 1H) 7.23-7.37 (m, 4H) 7.42 (dd, J=1.84, 0.61 Hz, 1H) 8.11-8.13 (m, 1H) 8.48 (d, J=8.67 Hz, 1H) 11.22 (s, 1H).

General Procedure for the Coupling of 5-(4-chlorophenyl)-1-(2,4-dichlorophenyl)-4-methyl-1H-pyrazole-3-carboxylic acid and diamines to yield amino-1H-pyrazole-3-carboxamides.

Benzotriazole-1-yl-oxytris(dimethylamino)phosphonium hexafluorophosphate (BOP) (1 eq) was added to a solution of 5-(4-chlorophenyl)-1-(2,4-dichlorophenyl)-4-methyl-1H-pyrazole-3-carboxylic acid (1 eq), and diamine (5 eq) in tetrahydrofuran (THF). The reaction mixture was stirred for 16 h. Ethyl acetate was added and the solution was washed with 2 N sodium hydroxide and brine. The organic layer was dried with magnesium sulfate. The solution was then filtered and concentrated in vacuo. The crude reaction material was then purified by silica gel column chromatography using 0-100% CMA 80/ethyl acetate to yield pure amino-1H-pyrazole-3-carboxamides.

N-{3-[(3-aminopropyl)(methyl)amino]propyl}-5-(4-chlorophenyl)-1-(2,4-dichlorophenyl)-4-methyl-1H-pyrazole-3-carboxamide: $^1$H NMR (300 MHz, CHLOROFORM-d) d ppm 1.53-1.69 (m, 2H) 1.77 (t, J=6.62 Hz, 2H) 2.15-2.23 (m, 3H) 2.34-2.50 (m, 7H) 2.66-2.75 (m, 2H) 3.45-3.53 (m, 2H) 7.03-7.09 (m, 2H) 7.23-7.35 (m, 3H) 7.43 (dd, J=2.05, 0.54 Hz, 1H) 7.75 (t, J=5.37 Hz, 1H).

N-{[4-(aminomethyl)phenyl]methyl}-5-(4-chlorophenyl)-1-(2,4-dichlorophenyl)-4-methyl-1H-pyrazole-3-carboxamide: $^1$H NMR (300 MHz, CHLOROFORM-d) d ppm 2.30-2.48 (m, 3H) 3.84 (s, 2H) 4.60 (d, J=6.08 Hz, 2H) 6.98-7.15 (m, 2H) 7.22-7.37 (m, 8H) 7.39-7.42 (m, 1H).

N-{[3-(aminomethyl)phenyl]methyl}-5-(4-chlorophenyl)-1-(2,4-dichlorophenyl)-4-methyl-1H-pyrazole-3-carboxamide: $^1$H NMR (300 MHz, CHLOROFORM-d) d ppm 2.31-2.47 (m, 3H) 3.85 (s, 2H) 4.62 (d, J=6.08 Hz, 2H) 6.98-7.14 (m, 2H) 7.19-7.35 (m, 8H) 7.37-7.42 (m, 1H).

General Procedure for the Conversion of amino-1H-pyrazole-3-carboxamides methanesulfonamido-1H-pyrazole-3-carboxamides.

Methanesulfonyl chloride (2 eq) was added to an amino-1H-pyrazole-3-carboxamide (1 eq), and triethylamine (TEA) (3 eq) in tertahydrofuran (THF). The reaction was stirred for 16 h. The reaction was concentrated in vacuo. The crude reaction material was then purified by silica gel column chromatography using 0-100% ethyl acetate/hexane to yield pure methanesulfonamido-1H-pyrazole-3-carboxamides.

5-(4-chlorophenyl)-1-(2,4-dichlorophenyl)-N-(7-methanesulfonamidoheptyl)-4-methyl-1H-pyrazole-3-carboxamide: $^1$H NMR (300 MHz, CHLOROFORM-d) d ppm 1.31-1.46 (m, 7H) 1.58 (br. s., 3H) 2.38 (br. s., 3H) 2.96 (br. s., 3H) 3.07-3.18 (m, 2H) 3.36-3.47 (m, 2H) 4.39 (br. s., 1H) 6.97 (br. s., 1H) 7.01-7.12 (m, 2H) 7.24-7.36 (m, 4H) 7.41-7.46 (m, 1H).

5-(4-chlorophenyl)-1-(2,4-dichlorophenyl)-4-methyl-N-[(1r,4r)-4-methanesulfonamido-cyclohexyl]-1H-pyrazole-3-carboxamide: $^1$H NMR (300 MHz, CHLOROFORM-d) d ppm 1.34-1.49 (m, 4H) 2.14 (d, J=9.80 Hz, 4H) 2.35-2.40 (m, 3H) 2.98-3.08 (m, 3H) 3.93 (d, J=7.91 Hz, 1H) 4.23 (d, J=7.49 Hz, 1H) 6.79 (d, J=8.19 Hz, 1H) 7.01-7.09 (m, 2H) 7.26-7.39 (m, 4H) 7.43 (d, J=0.66 Hz, 1H).

5-(4-chlorophenyl)-1-(2,4-dichlorophenyl)-N-{[4-(methanesulfonamidomethyl)cyclohexyl]methyl}-4-methyl-1H-pyrazole-3-carboxamide: $^1$H NMR (300 MHz, CHLOROFORM-d) d ppm 1.34-1.76 (m, 8H) 1.76-1.93 (m, 2H) 2.30-2.45 (m, 3H) 2.90-3.12 (m, 2H) 3.20-3.45 (m, 2H) 4.49-4.60 (m, 1H) 6.97-7.12 (m, 3H) 7.21-7.38 (m, 4H) 7.38-7.51 (m, 1H).

5-(4-chlorophenyl)-1-(2,4-dichlorophenyl)-4-methyl-N-{[(1s,4s)-4-(methanesulfonamidomethyl)cyclohexyl]methyl}-1H-pyrazole-3-carboxamide: $^1$H NMR (300 MHz, CHLOROFORM-d) d ppm 1.37-1.51 (m, 4H) 1.53-1.63 (m, 4H) 1.65-1.76 (m, 1H) 1.84 (d, J=7.02 Hz, 1H) 2.37 (s, 3H) 2.96 (s, 3H) 3.01-3.12 (m, 2H) 3.40 (s, 2H) 7.03-7.10 (m, 2H) 7.25-7.39 (m, 5H) 7.42-7.45 (m, 1H).

5-(4-chlorophenyl)-1-(2,4-dichlorophenyl)-N-{3-[(3-methanesulfonamidopropyl)(methyl)amino]propyl}-4-methyl-1H-pyrazole-3-carboxamide: $^1$H NMR (300 MHz, CHLOROFORM-d) d ppm 1.60-1.77 (m, 4H) 2.13 (s, 3H) 2.26-2.33 (m, 3H) 2.34-2.46 (m, 4H) 2.79-2.89 (m, 3H) 3.16 (t, J=5.93 Hz, 2H) 3.36-3.49 (m, 2H) 6.94-7.05 (m, 2H) 7.18-7.33 (m, 5H) 7.35-7.38 (m, 1H).

5-(4-chlorophenyl)-1-(2,4-dichlorophenyl)-N-{[4-(methanesulfonamidomethyl)phenyl]methyl}-4-methyl-1H-pyrazole-3-carboxamide: $^1$H NMR (300 MHz, CHLOROFORM-d) d ppm 2.39 (s, 3H) 2.88 (s, 3H) 4.29 (s, 2H) 4.52-4.76 (m, 3H) 7.02-7.10 (m, 2H) 7.19-7.46 (m, 10H).

5-(4-chlorophenyl)-1-(2,4-dichlorophenyl)-N-{[3-(methanesulfonamidomethyl)phenyl]methyl}-4-methyl-1H-pyrazole-3-carboxamide: $^1$H NMR (300 MHz, DICHLOROMETHANE-d$_2$) d ppm 2.36 (s, 3H) 2.87 (s, 3H) 4.30 (d, J=5.98 Hz, 2H) 4.59 (d, J=6.12 Hz, 3H) 5.33 (br. s., 1H) 7.10 (d, J=8.67 Hz, 2H) 7.20-7.54 (m, 10H).

General Procedure for the Conversion of amino-1H-pyrazole-3-carboxamides to sulfamoylamino-1H-pyrazole-3-carboxamides.

Amino-1H-pyrazole-3-carboxamides (1 eq), and sulfamide (5 eq) were heated in dioxane at 90° C. for 16 h. The solution was cooled and concentrated in vacuo. The crude reaction material was then purified by silica gel column chromatography using 0-100% ethyl acetate/hexane. The material was then dissolved in methanol. Water was added and pure sulfamoylamino-1H-pyrazole-3-carboxamides precipitated and was collected by filtration.

5-(4-chlorophenyl)-1-(2,4-dichlorophenyl)-4-methyl-N-[7-(sulfamoylamino)heptyl]-1H-pyrazole-3-carboxamide: $^1$H NMR (300 MHz, CHLOROFORM-d) d ppm 1.33-1.44 (m, 5H) 1.49-1.76 (m, 5H) 2.36 (s, 3H) 3.12 (td, J=6.96, 6.19 Hz, 2H) 3.33-3.49 (m, 2H) 4.47-4.53 (m, 1H) 4.71-4.87 (m, 2H) 6.93-7.11 (m, 3H) 7.21-7.38 (m, 4H) 7.38-7.45 (m, 1H).

5-(4-chlorophenyl)-1-(2,4-dichlorophenyl)-4-methyl-N-[(1r,4r)-4-(sulfamoylamino)cyclohexyl]-1H-pyrazole-3-carboxamide: $^1$H NMR (300 MHz, CHLOROFORM-d) d ppm 1.28-1.49 (m, 4H) 2.07-2.25 (m, 4H) 2.28-2.45 (m, 3H) 3.33 (br. s, 1H) 3.82-4.00 (m, 1H) 4.21 (d, J=7.72 Hz, 1H) 4.49 (s, 2H) 6.78 (d, J=8.19 Hz, 1H) 7.05 (d, J=8.38 Hz, 2H) 7.18-7.51 (m, 5H).

5-(4-chlorophenyl)-1-(2,4-dichlorophenyl)-4-methyl-N-({4-[(sulfamoylamino)methyl]cyclohexyl}methyl)-1H-pyrazole-3-carboxamide: $^1$H NMR (300 MHz, CHLOROFORM-d) d ppm 1.38-1.68 (m, 8H) 1.86 (br. s., 2H) 2.33-2.40 (m, 3H) 2.88-3.14 (m, 2H) 3.20-3.47 (m, 2H) 4.42 (d, J=5.79 Hz, 1H) 4.52-4.71 (m, 2H) 6.96-7.10 (m, 3H) 7.24-7.34 (m, 5H) 7.41-7.47 (m, 1H).

5-(4-chlorophenyl)-1-(2,4-dichlorophenyl)-4-methyl-N-{[(1s,4s)-4-[(sulfamoylamino)methyl]cyclohexyl]methyl}-1H-pyrazole-3-carboxamide: $^1$H NMR (300 MHz, CHLOROFORM-d) d ppm 1.36-1.66 (m, 8H) 1.82 (br. s., 2H) 2.26-2.47 (m, 3H) 3.05-3.12 (m, 2H) 3.35-3.42 (m, 2H) 4.37 (t, J=6.17 Hz, 1H) 4.52-4.60 (m, 2H) 6.96-7.09 (m, 3H) 7.25-7.35 (m, 5H) 7.42-7.45 (m, 1H).

5-(4-chlorophenyl)-1-(2,4-dichlorophenyl)-4-methyl-N-({4-[(sulfamoylamino)methyl]phenyl}methyl)-1H-pyrazole-3-carboxamide: $^1$H NMR (300 MHz, METHANOL-$d_4$) d ppm 2.31 (s, 3H) 4.18 (s, 2H) 4.54 (s, 2H) 7.17-7.22 (m, 2H) 7.29-7.59 (m, 9H).

5-(4-chlorophenyl)-1-(2,4-dichlorophenyl)-4-methyl-N-({3-[(sulfamoylamino)methyl]phenyl}methyl)-1H-pyrazole-3-carboxamide: $^1$H NMR (300 MHz, METHANOL-$d_4$) d ppm 2.32 (s, 3H) 4.19 (s, 2H) 4.55 (s, 2H) 7.12-7.63 (m, 11H).

1-{[5-(4-chlorophenyl)-1-(2,4-dichlorophenyl)-4-methyl-1H-pyrazol-3-yl]carbonyl}-4-phenylpiperidine-4-carboxylic acid A 2 M solution of oxalyl chloride in dichloromethane (3 eq., 0.19 mL, 0.377 mmol) was added to 5-(4-chlorophenyl)-1-(2,4-dichlorophenyl)-4-methyl-1H-pyrazole-3-carboxylic acid (1 eq., 48 mg, 0.126 mmol) in dichloromethane (5 mL). Next, 2 drops of anhydrous N,N-dimethylformamide was added the reaction was stirred for 2 h. The reaction was concentrated in vacuo. The reaction mixture was dissolved in dichloromethane (5 mL). Triethylamine (3 eq., 0.05 mL, 0.377 mmol) and 4-carboxy-4-phenylpiperidin-1-ium chloride (1.5 eq., 45.7 mg, 0.189 mmol) was added and the reaction was stirred for 16 h. The reaction was concentrated in vacuo. The crude reaction material was then purified by silica gel column chromatography using 0-10% methanol/dichloromethane with 1% acetic acid to yield pure 1-{[5-(4-chlorophenyl)-1-(2,4-dichlorophenyl)-4-methyl-1H-pyrazol-3-yl]carbonyl}-4-phenylpiperidine-4-carboxylic acid (48 mg, 67%). (77) $^1$H NMR (300 MHz, CHLOROFORM-d) d ppm 1.87-2.09 (m, 2H) 2.15 (s, 3H) 2.61 (t, J=16.18 Hz, 2H) 3.21 (t, J=12.03 Hz, 1H) 3.47 (t, J=11.94 Hz, 1H) 4.26 (d, J=13.61 Hz, 1H) 4.57 (d, J=13.56 Hz, 1H) 7.05 (d, J=8.34 Hz, 2H) 7.12-7.45 (m, 10H).

1-{[5-(4-chlorophenyl)-1-(2,4-dichlorophenyl)-4-methyl-1H-pyrazol-3-yl]carbonyl}-4-phenylpiperidine-4-carboxamide 1-{[5-(4-Chlorophenyl)-1-(2,4-dichlorophenyl)-4-methyl-1H-pyrazol-3-yl]carbonyl}-4-phenylpiperidine-4-carboxylic acid (1 eq., 12.7 mg, 0.024 mmol), ammonium chloride (10 eq., 12.7 mg, 0.24 mmol), benzotriazole-1-yl-oxytris (dimethylamino)phosphonium hexafluorophosphate (BOP) (1 eq, 10.5 mg, 0.024 mmol), and triethylamine (10.1 eq., 0.03 mL, 0.024 mmol) was stirred in tetrahydrofuran (5 mL) for 3 d. The reaction was concentrated in vacuo. The crude reaction material was then purified by silica gel column chromatography using 0-100% ethyl acetate/hexane to yield pure 1-{[5-(4-chlorophenyl)-1-(2,4-dichlorophenyl)-4-methyl-1H-pyrazol-3-yl]carbonyl}-4-phenylpiperidine-4-carboxamide (6 mg, 44%). $^1$H NMR (300 MHz, CHLOROFORM-d) d ppm 1.92-2.31 (m, 5H) 2.46 (d, J=13.94 Hz, 2H) 3.65 (t, J=10.36 Hz, 1H) 3.75-3.90 (m, 1H) 4.02 (d, J=13.38 Hz, 1H) 4.23 (d, J=13.00 Hz, 1H) 5.24 (br. s., 2H) 7.07 (d, J=8.38 Hz, 2H) 7.12-7.20 (m, 1H) 7.20-7.49 (m, 9H).

1-{[5-(4-chlorophenyl)-1-(2,4-dichlorophenyl)-4-methyl-1H-pyrazol-3-yl]carbonyl}-4-(ethylamino)piperidine-4-carboxamide 5-(4-Chlorophenyl)-1-(2,4-dichlorophenyl)-4-methyl-1H-pyrazole-3-carboxylic acid (1 eq, 20 mg, 0.052 mmol), triethylamine (3 eq, 0.02 mL, 0.157 mmol), 4-(ethylamino)-4-piperidinecarboxamide (1 eq, 9 mg, 0.052 mmol), and benzotriazole-1-yl-oxytris(dimethylamino)phosphonium hexafluorophosphate (BOP) (1 eq, 23 mg, 0.052 mmol) was stirred in tetrahydrofuran (5 mL) for 16 h. The reaction was concentrated in vacuo. The crude reaction material was then purified by silica gel column chromatography using 0-100% CMA 80/ethyl acetate and precipitated from ethyl acetate with hexane to yield pure 1-{[5-(4-chlorophenyl)-1-(2,4-dichlorophenyl)-4-methyl-1H-pyrazol-3-yl]carbonyl}-4-(ethylamino)piperidine-4-carboxamide (13 mg, 46%). $^1$H NMR (300 MHz, CHLOROFORM-d) d ppm 1.10 (t, J=6.97 Hz, 3H) 1.61-1.80 (m, 2H) 2.08-2.26 (m, 5H) 2.45-2.63 (m, 2H) 3.68 (td, J=8.85, 4.43 Hz, 2H) 3.96-4.19 (m, 2H) 5.40 (br. s., 1H) 7.07 (d, J=8.29 Hz, 2H) 7.12-7.19 (m, 1H) 7.20-7.36 (m, 3H) 7.44 (d, J=1.98 Hz, 1H).

1-{[1-(2,4-dichlorophenyl)-5-[4-(dimethylamino)phenyl]-4-methyl-1H-pyrazol-3-yl]carbonyl}-4-phenylpiperidin-4-ol Ethyl 1-(2,4-dichlorophenyl)-4-methyl-5-[(trifluoromethane)sulfonyloxy]-1H-pyrazole-3-carboxylate (1 eq., 253 mg, 0.566 mmol), sodium carbonate (2 eq, 120 mg, 1.13 mmol), tetrakis (triphenylphosphine)palladium(0) (0.10 eq, 65.3 mg, 0.057 mmol), and 4-(N,N-dimethylamino) phenylboronic acid (1.5 eq, 98.6 mg, 0.477 mmol) was heated to 80° C. in 1,2-dimethoxyethane for 16 h. The reaction is then cooled to rt. The reaction was concentrated in vacuo. The crude reaction material was then purified by silica gel column chromatography using 0-100% ethyl acetate/hexane to yield ethyl 1-(2,4-dichlorophenyl)-5-[4-(dimethylamino)phenyl]-4-methyl-1H-pyrazole-3-carboxylate (39 mg, 16%). $^1$H NMR (300 MHz, CHLOROFORM-d) d ppm 1.42 (td, J=7.02, 1.98 Hz, 3H) 2.23-2.40 (m, 3H) 2.79-3.01 (m, 6H) 4.31-4.53 (m, 2H) 6.50-6.65 (m, 2H) 6.97 (dd, J=8.62, 1.93 Hz, 2H) 7.13-7.41 (m, 3H).

Ethyl 1-(2,4-dichlorophenyl)-5-[4-(dimethylamino)phenyl]-4-methyl-1H-pyrazole-3-carboxylate (1 eq, 39 mg, 0.072 mmol) and lithium hydroxide (3 eq, 5.2 mg, 0.215 mmol) was heated at 65° C. in tetrahydrofuran (3 mL) and water (3 mL) for 16 h. The reaction was quenched with a small amount of 10% HCl. The reaction was concentrated in vacuo. The crude reaction material was then purified by silica gel column chromatography using 0-10% methanol/dichloromethane with 1% acetic acid to yield 1-(2,4-dichlorophenyl)-5-[4-(dimethylamino)phenyl]-4-methyl-1H-pyrazole-3-carboxylic acid (11 mg, 39%). $^1$H NMR (300 MHz, CHLOROFORM-d) d ppm 2.36 (s, 3H) 2.84-3.05 (m, 6H) 6.60 (d, J=7.35 Hz, 2H) 6.97 (d, J=7.44 Hz, 2H) 7.20-7.37 (m, 2H) 7.42 (br. s., 1H)

1-(2,4-dichlorophenyl)-5-[4-(dimethylamino)phenyl]-4-methyl-1H-pyrazole-3-carboxylic acid (1 eq, 10 mg, 0.026 mmol), 4-hydroxy-4-phenylpiperidine (1 eq, 4.5 mg, 0.026 mmol), benzotriazole-1-yl-oxytris(dimethylamino)phosphonium hexafluorophosphate (BOP) (1 eq., 11.3 mg, 0.026 mmol), and triethylamine (0.02 mL) were stirred in tetrahydrofuran (5 mL) for 16 h. The reaction was concentrated in vacuo. The crude reaction material was then purified by silica gel column chromatography using 0-100% ethyl acetate/hexane to yield pure 1-{[1-(2,4-dichlorophenyl)-5-[4-(dimethylamino)phenyl]-4-methyl-1H-pyrazol-3-yl]carbonyl}-4-phenylpiperidin-4-ol (7 mg, 50%). $^1$H NMR (300 MHz, CHLOROFORM-d) d ppm 1.73-1.95 (m, 2H) 2.09-2.29 (m, 5H) 2.85-3.04 (m, 3H) 3.34 (t, J=12.43 Hz, 1H) 3.66 (t, J=12.81 Hz, 1H) 4.34 (d, J=13.19 Hz, 1H) 4.74 (d, J=13.28 Hz, 1H) 6.61 (d, J=8.57 Hz, 2H) 6.99 (d, J=8.67 Hz, 2H) 7.09-7.57 (m, 8H).

1-{[5-(4-bromophenyl)-1-(2,4-dichlorophenyl)-4-methyl-1H-pyrazol-3-yl]carbonyl}-4-phenylpiperidine-4-carboxamide 5-(4-bromophenyl)-1-(2,4-dichlorophenyl)-4-methyl-1H-pyrazole-3-carboxylic acid (1 eq, 130 mg, 0.306 mmol), 4-carbamoyl-4-phenylpiperidin-1-ium trifluoroacetate (1.1 eq, 69 mg, 0.337 mmol), benzotriazole-1-yl-oxytris(dimethylamino)phosphonium hexafluorophosphate (BOP) (1.1 eq., 149 mg, 0.337 mmol), and triethylamine (3 eq, 0.13 mL, 0.92 mmol) was stirred in tetrahydrofuran (5 mL) for 6 h. The reaction was concentrated in vacuo. The crude reaction material was then purified by silica gel column chromatography using 0-100% ethyl acetate/hexane to yield pure 1-{[5-(4-bromophenyl)-1-(2,4-dichlorophenyl)-4-methyl-1H-pyrazol-3-yl]carbonyl}-4-phenylpiperidine-4-carboxamide (98 mg, 52%). $^1$H NMR (300 MHz, CHLOROFORM-d) d ppm 2.10 (dd, J=9.75, 3.63 Hz, 1H) 2.18 (s, 3H) 2.20-2.28 (m, 1H) 2.46 (d, J=14.03 Hz, 2H) 3.65 (t, J=10.31 Hz, 1H) 3.75-3.88 (m, 1H) 3.95-4.07 (m, 1H) 4.15-4.28 (m, 1H) 5.17-5.50 (m, 2H) 7.00 (d, J=8.38 Hz, 2H) 7.12-7.50 (m, 10H).

tert-Butyl N-(1-{[5-(4-chlorophenyl)-1-(2,4-dichlorophenyl)-4-methyl-1H-pyrazol-3-yl]carbonyl}-4-phenylpiperidin-4-yl)carbamate 5-(4-Chlorophenyl)-1-(2,4-dichlorophenyl)-4-methyl-1H-pyrazole-3-carboxylic acid (1 eq., 201 mg, 0.53 mmol), triethylamine (3 eq, 0.22 mL, 0.157 mmol), tert-butyl N-(4-phenyl piperidin-4-yl)carbamate (1 eq, 146 mg, 0.53 mmol), and Benzotriazole-1-yl-oxytris(dimethylamino)phosphonium hexafluorophosphate (BOP) (1 eq, 233 mg, 0.53 mmol) was stirred in tetrahydrofuran (10 mL) for 16 h. The reaction was concentrated in vacuo. The crude reaction material was then purified by silica gel column chromatography using 0-100% ethyl acetate/hexane to yield pure tert-butyl N-(1-{[5-(4-chlorophenyl)-1-(2,4-dichlorophenyl)-4-methyl-1H-pyrazol-3-yl]carbonyl}-4-phenylpiperidin-4-yl)carbamate (295 mg, 87%). $^1$H NMR (300 MHz, CHLOROFORM-d) d ppm 1.37 (br. s., 9H) 2.11 (dd, J=12.67, 4.00 Hz, 2H) 2.21 (s, 3H) 2.24-2.34 (m, 1H) 2.34-2.56 (m, 1H) 3.26 (t, J=12.01 Hz, 1H) 3.56 (t, J=12.39 Hz, 1H) 4.32 (d, J=13.75 Hz, 1H) 4.64 (d, J=13.56 Hz, 1H) 4.96 (br. s., 1H) 7.08 (d, J=8.38 Hz, 2H) 7.13-7.49 (m, 10H).

1-{[5-(4-chlorophenyl)-1-(2,4-dichlorophenyl)-4-methyl-1H-pyrazol-3-yl]carbonyl}-4-phenylpiperidin-4-amine tert-Butyl N-(1-{[5-(4-chlorophenyl)-1-(2,4-dichlorophenyl)-4-methyl-1H-pyrazol-3-yl]carbonyl}-4-phenylpiperidin-4-yl)carbamate (1 eq, 243 mg, 0.380 mmol) was stirred in dichloromethane (7 mL) and trifluoroacetic acid (3 mL) for 16 h. The reaction was concentrated in vacuo. The crude reaction material was then purified by silica gel column chromatography using 0-50% CMA 80/ethyl acetate to yield pure 1-{[5-(4-chlorophenyl)-1-(2,4-dichlorophenyl)-4-methyl-1H-pyrazol-3-yl]carbonyl}-4-phenylpiperidin-4-amine (178 mg, 87%). $^1$H NMR (300 MHz, CHLOROFORM-d) d ppm 1.64-1.95 (m, 2H) 2.10-2.29 (m, 5H) 3.50-3.66 (m, 1H) 3.70-3.88 (m, 1H) 4.03-4.19 (m, 1H) 4.42 (d, J=13.28 Hz, 1H) 7.04-7.10 (m, 2H) 7.13-7.20 (m, 1H) 7.20-7.40 (m, 6H) 7.40-7.50 (m, 3H).

N-(1-{[5-(4-chlorophenyl)-1-(2,4-dichlorophenyl)-4-methyl-1H-pyrazol-3-yl]carbonyl}-4-phenylpiperidin-4-yl)acetamide 1-{[5-(4-Chlorophenyl)-1-(2,4-dichlorophenyl)-4-methyl-1H-pyrazol-3-yl]carbonyl}-4-phenylpiperidin-4-amine (1 eq, 35.3 mg, 0.066 mmol) was stirred in a mixture of acetic anhydride (2 mL) and pyridine (2 mL) for 16 h. The reaction was concentrated in vacuo. The crude reaction material was then purified by silica gel column chromatography using 0-100% ethyl acetate/hexane to yield pure N-(1-{[5-(4-chlorophenyl)-1-(2,4-dichlorophenyl)-4-methyl-1H-pyrazol-3-yl]carbonyl}-4-phenylpiperidin-4-yl)acetamide (27 mg, 71%). $^1$H NMR (300 MHz, CHLOROFORM-d) d ppm 2.01 (s, 3H) 2.05-2.19 (m, 2H) 2.21 (s, 3H) 2.34 (d, J=14.60 Hz, 1H) 2.66 (d, J=13.85 Hz, 1H) 3.15-3.34 (m, 1H) 3.52 (t, J=11.68 Hz, 1H) 4.26 (d, J=13.75 Hz, 1H) 4.54 (d, J=13.75 Hz, 1H) 6.10 (s, 1H) 7.03-7.11 (m, 2H) 7.14-7.19 (m, 1H) 7.19-7.41 (m, 8H) 7.44 (d, J=2.17 Hz, 1H).

N-(1-{[5-(4-chlorophenyl)-1-(2,4-dichlorophenyl)-4-methyl-1H-pyrazol-3-yl]carbonyl}-4-phenylpiperidin-4-yl)methanesulfonamide 1-{[5-(4-Chlorophenyl)-1-(2,4-dichlorophenyl)-4-methyl-1H-pyrazol-3-yl]carbonyl}-4-phenylpiperidin-4-amine (1 eq, 36.5 mg, 0.068 mmol), methanesulfonyl chloride (2 eq, 0.01 mL, 0.135 mmol), and triethylamine (3 eq, 0.03 mL, 0.203 mmol) was stirred in tetrahydrofuran for 16 h. The reaction was concentrated in vacuo. The crude reaction material was then purified by silica gel column chromatography using 0-100% ethyl acetate/hexane to yield pure N-(1-{[5-(4-chlorophenyl)-1-(2,4-dichlorophenyl)-4-methyl-1H-pyrazol-3-yl]carbonyl}-4-phenylpiperidin-4-yl)methanesulfonamide (27 mg, 65%). $^1$H NMR (300 MHz, CHLOROFORM-d) d ppm 2.18 (d, J=4.52 Hz, 6H) 2.21-2.37 (m, 2H) 2.39-2.61 (m, 2H) 3.65 (t, J=10.69 Hz, 1H) 3.86 (t, J=10.93 Hz, 1H) 4.07-4.20 (m, 2H) 4.29 (d, J=13.75 Hz, 1H) 5.30 (s, 1H) 7.03-7.11 (m, 2H) 7.15-7.21 (m, 1H) 7.21-7.38 (m, 4H) 7.38-7.47 (m, 2H) 7.47-7.55 (m, 2H).

4-[1-(2,4-dichlorophenyl)-3-[(4-hydroxy-4-phenylpiperidin-1-yl)carbonyl]-4-methyl-1H-pyrazol-5-yl]benzonitrile Nitrogen gas was bubbled through a solution of 1-{[5-(4-bromophenyl)-1-(2,4-dichlorophenyl)-4-methyl-1H-pyrazol-3-yl]carbonyl}-4-phenylpiperidin-4-ol (1 eq., 45 mg, 0.077 mmol), $K_4[Fe(CN)_6] \cdot 3H_2O$ (0.22 eq., 7.5 mg, 0.017 mmol), sodium carbonate (1 eq., 8.1 mg, 0.017 mmol), and palladium(II) acetate (0.10 eq., 1.7 mg, 0.008 mmol) in N,N-dimethylacetamide (2 mL) for 1 min. The solution is capped and stirred at 120° C. for 16 h. The reaction was concentrated in vacuo. The crude reaction material was then purified by silica gel column chromatography using 0-100% ethyl acetate/hexane to yield pure 4-[1-(2,4-dichlorophenyl)-3-[(4-hydroxy-4-phenylpiperidin-1-yl)carbonyl]-4-methyl-1H-pyrazol-5-yl]benzonitrile (4 mg, 10%). $^1$H NMR (300 MHz, CHLOROFORM-d) d ppm 1.75-1.94 (m, 2H) 2.07-2.32 (m, 5H) 3.25-3.43 (m, 1H) 3.55-3.76 (m, 1H) 4.31 (d, J=12.90 Hz, 1H) 4.73 (d, J=13.00 Hz, 1H) 7.01 (d, J=8.48 Hz, 2H) 7.08-7.57 (m, 10H).

3-tert-butyl-1-(1-{[5-(4-chlorophenyl)-1-(2,4-dichlorophenyl)-4-methyl-1H-pyrazol-3-yl]carbonyl}-4-phenylpiperidin-4-yl)urea 1-{[5-(4-Chlorophenyl)-1-(2,4-dichlorophenyl)-4-methyl-1H-pyrazol-3-yl]carbonyl}-4-phenylpiperidin-4-amine (1 eq, 39.3 mg, 0.073 mmol), tert-butyl isocyanate (1.5 eq, 0.013 mL, 0.109 mmol), and triethylamine (3.0 eq, 0.03 mL, 0.218 mmol) was stirred in dichloromethane (5 mL) for 16 h. Next, tetrahydrofuran (5 mL) and an additional 0.02 mL of tert-butyl isocyanate were added and the reaction was stirred for 16 h Finally, the reaction was heated to 40° C. for 16 h. The reaction was concentrated in vacuo. The crude reaction material was then purified by silica gel column chromatography using 0-100% ethyl acetate/hexane to yield pure 3-tert-butyl-1-(1-{[5-(4-chlorophenyl)-1-(2,4-dichlorophenyl)-4-methyl-1H-pyrazol-3-yl]carbonyl}-4-phenylpiperidin-4-yl)urea (21 mg, 45%). $^1$H NMR (300 MHz, CHLOROFORM-d) d ppm 1.15 (s, 9H) 1.93-2.17 (m, 4H) 2.20 (s, 3H) 2.42 (br. s., 1H) 3.13-3.35 (m, 1H) 3.58 (br. s., 1H) 4.25 (br. s., 1H) 4.44 (s, 1H) 4.52-4.69 (m, 1H) 5.13 (s, 1H) 7.03-7.10 (m, 2H) 7.13-7.37 (m, 7H) 7.38-7.46 (m, 3H).

tert-butyl 4-[5-(4-chlorophenyl)-1-(2,4-dichlorophenyl)-4-methyl-1H-pyrazole-3-amido]piperidine-1-carboxylate Benzotriazole-1-yl-oxytris(dimethylamino)phosphonium-hexafluorophosphate (BOP) (1 eq, 490 mg, 1.11 mmol) was added to a solution of 5-(4-chlorophenyl)-1-(2,4-dichlorophenyl)-4-methyl-1H-pyrazole-3-carboxylic acid (1 eq, 422 mg, 1.11 mmol), tert-butyl 4-amino-1-piperidinecarboxylate (1 eq, 222 mg, 1.11 mmol), and triethylamine (3 eq., 0.46 mL, 3.32 mmol) in tetrahydrofuran (5 mL). The reaction mixture was stirred for 16 h. The reaction was concentrated in vacuo. The crude reaction material was then purified by silica gel column chromatography using 0-100% ethyl acetate/hexane to yield pure tert-butyl 4-[5-(4-chlorophenyl)-1-(2,4-dichlorophenyl)-4-methyl-1H-pyrazole-3-amido]piperidine-1-carboxylate (548 mg, 88%). $^1$H NMR (300 MHz, CHLOROFORM-d) d ppm 1.33-1.51 (m, 9H) 1.93-2.10 (m, 2H) 2.37 (s, 3H) 2.91 (t, J=11.82 Hz, 2H) 3.89-4.23 (m, 2H) 6.84 (d, J=8.19 Hz, 1H) 7.00-7.12 (m, 2H) 7.19-7.36 (m, 4H) 7.43 (d, J=1.32 Hz, 1H).

5-(4-chlorophenyl)-1-(2,4-dichlorophenyl)-4-methyl-N-(piperidin-4-yl)-1H-pyrazole-3-carboxamide tert-Butyl-4-[5-(4-chlorophenyl)-1-(2,4-dichlorophenyl)-4-methyl-1H-pyrazole-3-amido]piperidine-1-carboxylate (1 eq, 531 mg, 0.941 mmol) was stirred in dichloromethane (4 mL) and trifluoroacetic acid (1 mL) for 16 h. The reaction was concentrated in vacuo. The crude reaction material was then purified by silica gel column chromatography using 0-100% CMA 80/ethyl acetate to yield pure 5-(4-chlorophenyl)-1-(2,4-dichlorophenyl)-4-methyl-N-(piperidin-4-yl)-1H-pyrazole-3-carboxamide (415 mg, 95%). $^1$H NMR (300 MHz, CHLOROFORM-d) d ppm 1.44 (qd, J=11.81, 3.86 Hz, 2H) 1.92-2.08 (m, 2H) 2.37 (s, 3H) 2.64-2.85 (m, 2H) 2.98-3.21 (m, 2H) 3.92-4.19 (m, 1H) 6.85 (d, J=8.29 Hz, 1H) 7.06 (d, J=8.38 Hz, 2H) 7.28 (s, 4H) 7.43 (s, 1H).

N-(1-acetylpiperidin-4-yl)-5-(4-chlorophenyl)-1-(2,4-dichlorophenyl)-4-methyl-1H-pyrazole-3-carboxamide tert-Butyl-4-[5-(4-chlorophenyl)-1-(2,4-dichlorophenyl)-4-methyl-1H-pyrazole-3-amido]piperidine-1-carboxylate (1 eq, 34 mg, 0.073 mmol) was stirred in pyridine (1 mL) and acetic anhydride (1 mL) for 16 h. The reaction was concentrated in vacuo. The crude reaction material was purified by silica gel column chromatography using 0-100% ethyl acetate/hexane to yield pure N-(1-acetylpiperidin-4-yl)-5-(4-chlorophenyl)-1-(2,4-dichloro-phenyl)-4-methyl-1H-pyrazole-3-carboxamide (30 mg, 81%). $^1$H NMR (300 MHz, CHLOROFORM-d) d ppm 1.28-1.49 (m, 2H) 1.87-2.13 (m, 5H) 2.30 (s, 3H) 2.62-2.82 (m, 1H) 3.05-3.24 (m, 1H) 3.75 (d, J=13.56 Hz, 1H) 3.98-4.25 (m, 1H) 4.49 (d, J=13.37 Hz, 1H) 6.80 (d, J=8.01 Hz, 1H) 6.99 (d, J=8.48 Hz, 2H) 7.13-7.29 (m, 4H) 7.36 (d, J=1.51 Hz, 1H).

5-(4-chlorophenyl)-1-(2,4-dichlorophenyl)-N-(1-methanesulfonylpiperidin-4-yl)-4-methyl-1H-pyrazole-3-carboxamide Methanesulfonyl chloride (2 eq., 0.01 mL, 0.15 mmol) was added to tert-Butyl 4-[5-(4-chlorophenyl)-1-(2,4-dichlorophenyl)-4-methyl-1H-pyrazole-3-amido]piperidine-1-carboxylate (1 eq., 35 mg, 0.076 mmol) and triethyamine (3 eq., 0.03 mL, 0.227 mmol) in tetrahydrofuran (2 mL). The reaction was stirred for 16 h. The reaction was concentrated in vacuo. The crude reaction material was then purified by silica gel column chromatography using 0-100% ethyl acetate/hexane to yield pure 5-(4-chlorophenyl)-1-(2,4-dichlorophenyl)-N-(1-methanesulfonyl-piperidin-4-yl)-4-methyl-1H-pyrazole-3-carboxamide (36 mg, 87%). $^1$H NMR (300 MHz, CHLOROFORM-d) d ppm 1.53-1.78 (m, 2H) 2.06-2.22 (m, 2H) 2.37 (s, 3H) 2.67-3.00 (m, 5H) 3.82 (d, J=12.24 Hz, 2H) 4.01-4.17 (m, 1H) 6.88 (d, J=8.01 Hz, 1H) 7.07 (s, 2H) 7.19-7.36 (m, 4H) 7.43 (d, J=1.70 Hz, 1H).

1-N-tert-butyl-4-C-5-(4-chlorophenyl)-1-(2,4-dichlorophenyl)-4-methyl-1H-pyrazole-3-piperidine-1,4-diamido tert-Butyl 4-[5-(4-chlorophenyl)-1-(2,4-dichlorophenyl)-4-methyl-1H-pyrazole-3-amido]piperidine-1-carboxylate (1 eq, 38 mg, 0.082 mmol), tert-butyl isocyanate (1.5 eq, 0.014 mL, 0.123 mmol), and triethylamine (3 eq, 0.034 mL, 0.246 mmol) were stirred in dichloromethane for 16 h. The reaction was concentrated in vacuo. The crude reaction material was purified by silica gel column chromatography using 0-100% ethyl acetate/hexane to yield pure 1-N-tert-butyl-4-C-5-(4-chlorophenyl)-1-(2,4-dichlorophenyl)-4-methyl-1H-pyrazole-3-piperidine-1,4-diamido (42 mg, 91%). $^1$H NMR (300 MHz, CHLOROFORM-d) d ppm 1.27 (d, J=7.16 Hz, 9H) 1.40-1.73 (m, 2H) 2.05 (s, 2H) 2.37 (s, 2H) 2.92 (t, J=11.44 Hz, 2H) 3.87 (d, J=13.37 Hz, 2H) 4.00-4.18 (m, 1H) 4.33 (s, 1H) 6.84 (d, J=7.91 Hz, 1H) 7.05 (d, J=8.48 Hz, 2H) 7.20-7.35 (m, 4H) 7.42 (s, 1H).

General Preparation of Other Diamido Compounds.

5-(4-chlorophenyl)-1-(2,4-dichlorophenyl)-4-methyl-N-(piperidin-4-yl)-1H-pyrazole-3-carboxamide (1 eq) was stirred with triethylamine (3 eq) and the appropriate isocyanate (1.5 eq) in THF. The mixture was concentrated in vacuo. The crude reaction material was then purified by silca gel chromatography using 1-100% ethyl acetate/hexanes to give the desired product.

4-C-5-(4-chlorophenyl)-1H-pyrazole-3-1-N-ethylpiperidine-1,4-diamido. Reaction yield was 97%. $^1$H NMR (300 MHz, chloroform-d) δ ppm 1.15 (t, J=7.21 Hz, 3H), 1.35-1.60 (m, 2H), 1.93-2.14 (m, 2H), 2.38 (s, 3H), 2.97 (t, J=11.54 Hz, 2H), 3.16-3.38 (m, 2H), 3.94 (d, J=13.47 Hz, 2H), 4.04-4.25 (m, 1H), 4.46 (br s, 1H), 6.87 (d, J=8.01 Hz, 1H), 7.08 (s, 2H), 7.23-7.37 (m, 4H), 7.44 (d, J=1.22 Hz, 1H); [M+H]+534.4.

4-C-5-(4-Chlorophenyl)-1-(2,4-dichlorophenyl)-4-methyl-1H-pyrazole-3-1-N-(propan-2-yl)piperidine-1,4-diamido. Reaction yield was 99%. $^1$H NMR (300 MHz, chloroform-d) δ ppm 1.16 (d, J=6.50 Hz, 6H), 1.49 (dd, J=11.68, 3.11 Hz, 2H), 1.98-2.11 (m, 2H), 2.38 (s, 3H), 2.95 (t, J=11.68 Hz, 2H), 3.86-4.02 (m, 3H), 4.11 (dd, J=13.70, 6.92 Hz, 1H), 4.27 (d, J=7.16 Hz, 1H), 6.86 (d, J=7.91 Hz, 1H), 7.07 (d, J=8.38 Hz, 2H), 7.25-7.36 (m, 4H), 7.44 (s, 1H); [M+H]+ 548.5.

4-C-5-(4-Chlorophenyl)-1-(2,4-dichlorophenyl)-4-methyl-1H-pyrazole-3-1-N-propylpiperidine-1,4-diamido. Reaction yield was 95%. $^1$H NMR (300 MHz, chloroform-d) δ ppm 0.86-0.98 (m, 3H), 1.43-1.60 (m, 4H), 1.94-2.13 (m, 2H), 2.38 (s, 3H), 2.97 (t, J=11.77 Hz, 2H), 3.20 (q, J=6.69 Hz, 2H), 3.94 (d, J=13.37 Hz, 2H), 4.09 (d, J=6.78 Hz, 1H), 4.51 (br s, 1H), 6.87 (d, J=8.01 Hz, 1H), 7.07 (d, J=8.29 Hz, 2H), 7.23-7.37 (m, 4H), 7.44 (s, 1H); [M+H]+ 548.6.

1-N-Butyl-4-C-5-(4-chlorophenyl)-1-(2,4-dichlorophenyl)-4-methyl-1H-pyrazole-3-piperidine-1,4-diamido. Reaction yield was 76%. $^1$H NMR (300 MHz, chloroform-d) δ ppm 0.94 (t, J=7.16 Hz, 3H), 1.28-1.41 (m, 2H), 1.42-1.58 (m, 4H), 1.95-2.12 (m, 2H), 2.38 (s, 3H), 2.97 (t, J=12.24 Hz, 2H), 3.16-3.33 (m, 2H), 3.94 (d, J=13.37 Hz, 2H), 4.03-4.23 (m, 1H), 4.47 (br s, 1H), 6.86 (d, J=7.91 Hz, 1H), 7.07 (d, J=8.29 Hz, 2H), 7.23-7.36 (m, 4H), 7.44 (s, 1H); [M+H]+ 562.4.

Ethyl 4-[5-(4-Chlorophenyl)-1-(2,4-dichlorophenyl)-4-methyl-1H-pyrazole-3-amido]piperidine-1-carboxylate. Reaction yield was 76%. $^1$H NMR (300 MHz, chloroform-d) δ ppm 1.27 (d, J=14.22 Hz, 3H), 1.47 (dd, J=11.63, 3.44 Hz, 2H), 1.93-2.14 (m, 2H), 2.38 (s, 3H), 2.98 (br s, 2H), 4.14 (q, J=6.97 Hz, 4H), 6.86 (d, J=8.10 Hz, 1H), 7.06 (s, 2H), 7.22-7.38 (m, 4H), 7.44 (s, 1H); [M+H]+ 535.3.

General Procedure for the Conversion of 4-nitrophenyl 4-[5-(4-chlorophenyl)-1-(2,4-dichlorophenyl)-4-methyl-1H-pyrazole-3-amido]piperidine-1-carboxylate into other carboxylates.

5-(4-Chlorophenyl)-1-(2,4-dichlorophenyl)-4-methyl-N-(piperidin-4-yl)-1H-pyrazole-3-carboxamide (1 eq, 61 mg, 0.132 mmol), p-nitrophenyl chloroformate (1.1 eq, 29 mg, 0.144 mmol), and triethylamine (3 eq, 0.06 mL, 0.395 mmol) were stirred for 16 h in THF (2 mL). The reaction was concentrated in vacuo. The crude material was purified by column chromatography 0-100% ethyl acetate/hexanes to yield 62 mg (75%) of desired product 4-nitrophenyl 4-[5-(4-chlorophenyl)-1-(2,4-dichlorophenyl)-4-methyl-1H-pyrazole-3-amido]piperidine-1-carboxylate. $^1$H NMR (300 MHz, CHLOROFORM-d) δ ppm 1.54-1.74 (m, 2H) 2.18 (br s, 2H) 2.42 (s, 3H) 3.04-3.38 (m, 2H) 4.21-4.43 (m, 3H) 6.95 (d, J=7.91 Hz, 1H) 7.10 (d, J=8.29 Hz, 2H) 7.30-7.41 (m, 5H) 7.47 (s, 1H) 8.29 (d, J=9.04 Hz, 2H); [M+H]+ 628.7.

To 4-nitrophenyl 4-[5-(4-chlorophenyl)-1-(2,4-dichlorophenyl)-4-methyl-1H-pyrazole-3-amido]piperidine-1-carboxylate (0.02 mmol, 1 eq.) and appropriate alcohol (0.5 mL) in THF (2 mL) was added sodium hydride 60% dispersion in mineral oil (4 mg, 0.1 mmol, 5 eq.). The reaction was stirred for 16 h and quenched with acetic acid. The reaction was concentrated in vacuo. The crude material was purified by column chromatography 0-100% ethyl acetate/hexanes to yield desired product.

Propan-2-yl 4-[5-(4-chlorophenyl)-1-(2,4-dichlorophenyl)-4-methyl-1H-pyrazole-3-amido]piperidine-1-carboxylate. Reaction proceeded in 46% yield. $^1$H NMR (300 MHz, CHLOROFORM-d) δ ppm 1.17 (d, J=6.22 Hz, 6H) 1.28-1.46 (m, 2H) 1.87-2.02 (m, 2H) 2.30 (s, 3H) 2.87 (t, J=11.87 Hz, 2H) 3.93-4.17 (m, 3H) 4.84 (dt, J=12.43, 6.22 Hz, 1H) 6.78 (d, J=8.10 Hz, 1H) 6.99 (d, J=8.38 Hz, 2H) 7.20-7.27 (m, 3H) 7.35 (s, 1H); [M+H]+ 549.4.

Butyl 4-[5-(4-chlorophenyl)-1-(2,4-dichlorophenyl)-4-methyl-1H-pyrazole-3-amido]piperidine-1-carboxylate. Reaction proceeded in 51% yield. $^1$H NMR (300 MHz, CHLOROFORM-d) δ ppm 0.81-0.94 (m, 3H) 1.25-1.65 (m, 6H) 1.96 (d, J=12.72 Hz, 2H) 2.30 (s, 3H) 2.89 (t, J=12.15 Hz, 2H) 3.93-4.18 (m, 5H) 6.78 (d, J=8.10 Hz, 1H) 6.99 (d, J=8.38 Hz, 2H) 7.20-7.27 (m, 3H) 7.36 (d, J=1.51 Hz, 1H); [M+H]+ 563.5.

Methyl 4-[5-(4-chlorophenyl)-1-(2,4-dichlorophenyl)-4-methyl-1H-pyrazole-3-amido]piperidine-1-carboxylate. Reaction proceeded in 78% yield. $^1$H NMR (300 MHz, CHLOROFORM-d) δ ppm 1.37-1.52 (m, 2H) 1.96-2.11 (m, 3H) 2.37 (s, 3H) 2.97 (t, J=12.15 Hz, 2H) 3.69 (s, 3H) 3.98-4.26 (m, 3H) 6.85 (d, J=8.01 Hz, 1H) 7.06 (d, J=8.29 Hz, 2H) 7.27-7.34 (m, 3H) 7.43 (s, 1H); [M+H]+ 521.7.

Ethyl 4-[5-(4-chlorophenyl)-1-(2,4-dichlorophenyl)-4-methyl-1H-pyrazole-3-amido]piperidine-1-carboxylate. Reaction proceeded in 88% yield. $^1$H NMR (300 MHz, CHLOROFORM-d) δ ppm 0.90-0.99 (m, 3H) 1.40-1.53 (m, 2H) 1.60-1.72 (m, 2H) 2.02 (d, J=14.13 Hz, 2H) 2.37 (s, 3H) 2.96 (t, J=12.15 Hz, 2H) 4.03 (t, J=6.64 Hz, 2H) 4.07-4.25 (m, 3H) 6.85 (d, J=8.10 Hz, 1H) 7.06 (d, J=8.38 Hz, 2H) 7.27-7.34 (m, 3H) 7.43 (d, J=1.51 Hz, 1H); [M+H]+ 549.7.

tert-Butyl N-(1-{[5-(4-chlorophenyl)-1-(2,4-dichlorophenyl)-4-methyl-1H-pyrazol-3-yl]carbonyl}piperidin-4-yl)carbamate To 5-(4-chlorophenyl)-1-(2,4-dichlorophenyl)-4-methyl-1H-pyrazole-3-carboxylic acid (1 eq, 200 mg, 0.52 mmol), tert-butyl 4-piperidinylcarbamate (1 eq, 105 mg, 0.052 mmol), and triethylamine (3 eq, 0.22 mL, 1.57 mmol) was added (Benzotriazol-1-yloxy)tris(dimethylamino)phosphonium hexafluorophosphate (1 eq, 232 mg, 0.52 mmol). The reaction was stirred 16 h and then concentrated in vacuo. The crude material was purified by column chromatography 0-100% ethyl acetate/hexanes to yield 277 mg (93%) of desired product. $^1$H NMR (300 MHz, CHLOROFORM-d) δ ppm 1.45 (s, 11H) 1.95-2.10 (m, 2H) 2.14-2.25 (m, 3H) 2.97 (br. s., 1H) 3.25 (d, J=7.63 Hz, 1H) 3.66-3.82 (m, 1H) 4.31 (d, J=13.37 Hz, 1H) 4.49 (d, J=5.84 Hz, 1H) 4.66 (d, J=13.09 Hz, 1H) 7.03-7.10 (m, 2H) 7.12-7.18 (m, 1H) 7.21-7.34 (m, 3H) 7.45 (d, J=2.07 Hz, 1H); [M+Na]$^+$ 587.4.

1-{[5-(4-Chlorophenyl)-1-(2,4-dichlorophenyl)-4-methyl-1H-pyrazol-3-yl]carbonyl}piperidin-4-amine tert-Butyl N-(1-{[5-(4-chlorophenyl)-1-(2,4-dichlorophenyl)-4-methyl-1H-pyrazol-3-yl]carbonyl}piperidin-4-yl) carbamate (194 mg) was stirred in dichloromethane (7 mL) and trifluoroacetic acid (3 mL) for 4 h. The reaction was concentrated in vacuo and dissolved in ethyl acetate. The solution was washed with 3.8 N NaOH and brine. The organic layer was dried with magnesium sulfate. The reaction was concentrated in vacuo to yield 0.15 g (94%) of desired product. $^1$H NMR (300 MHz, CHLOROFORM-d) δ ppm 1.31-1.52 (m, 2H) 1.83-2.02 (m, 2H) 2.14-2.26 (m, 3H) 2.84-3.07 (m, 2H) 3.11-3.33 (m, 1H) 4.31 (d, J=13.47 Hz, 1H) 4.66 (d, J=13.19 Hz, 1H) 7.07 (d, J=8.38 Hz, 2H) 7.14-7.20 (m, 1H) 7.21-7.34 (m, 3H) 7.44 (d, J=1.98 Hz, 1H); [M+H]$^+$ 463.4.

General Procedure for Making Ureas from 1-{[5-(4-chlorophenyl)-1-(2,4-dichlorophenyl)-4-methyl-1H-pyrazol-3-yl]carbonyl}piperidin-4-amine.

1-{[5-(4-Chlorophenyl)-1-(2,4-dichlorophenyl)-4-methyl-1H-pyrazol-3-yl]carbonyl}piperidin-4-amine (20 mg, 0.043 mmol, 1 eq.), triethylamine (0.02 mL, 0.129 mmol, 3 eq.), and the appropriate isocyanate (0.065 mmol, 1.5 eq.) were stirred in dichloromethane (2 mL) for 16 h. The reaction was concentrated in vacuo. The crude material was purified by column chromatography 0-100% ethyl acetate/hexanes to yield desired product.

1-(1-{[5-(4-Chlorophenyl)-1-(2,4-dichlorophenyl)-4-methyl-1H-pyrazol-3-yl]carbonyl}piperidin-4-yl)-3-(propan-2-yl)urea. Reaction proceeded in 70% yield. $^1$H NMR (300 MHz, CHLOROFORM-d) ppm 1.12 (d, J=6.50 Hz, 6H) 1.31-1.50 (m, 2H) 1.93-2.09 (m, 2H) 2.17 (s, 3H) 2.97 (t, J=11.68 Hz, 1H) 3.24 (t, J=12.01 Hz, 1H) 3.85 (dd, J=14.27, 7.11 Hz, 2H) 4.19-4.42 (m, 3H) 4.64 (d, J=13.19 Hz, 1H) 7.06 (d, J=8.29 Hz, 2H) 7.11-7.18 (m, 1H) 7.20-7.34 (m, 3H) 7.44 (d, J=1.60 Hz, 1H); [M+H]$^+$ 548.4.

1-(1-{[5-(4-Chlorophenyl)-1-(2,4-dichlorophenyl)-4-methyl-1H-pyrazol-3-yl]carbonyl}piperidin-4-yl)-3-propylurea. Reaction proceeded in 52% yield. $^1$H NMR (300 MHz, CHLOROFORM-d) ppm 0.83-0.97 (m, 3H) 1.34-1.55 (m, 4H) 1.96-2.10 (m, 2H) 2.12-2.26 (m, 3H) 2.97 (t, J=11.54 Hz, 1H) 3.09 (q, J=6.50 Hz, 2H) 3.24 (t, J=11.96 Hz, 1H) 3.79-3.99 (m, 1H) 4.26 (d, J=13.38 Hz, 1H) 4.33-4.51 (m, 2H) 4.64 (d, J=13.28 Hz, 1H) 7.06 (d, J=8.29 Hz, 2H) 7.12-7.18 (m, 1H) 7.20-7.34 (m, 3H) 7.44 (d, J=1.79 Hz, 1H); [M+11]$^+$ 548.4.

3-Butyl-1-(1-{[5-(4-chlorophenyl)-1-(2,4-dichlorophenyl)-4-methyl-1H-pyrazol-3-yl]carbonyl}piperidin-4-yl) urea. Reaction proceeded in 63% yield. $^1$H NMR (300 MHz, CHLOROFORM-d) δ ppm 0.85-0.96 (m, 3H) 1.26-1.50 (m, 6H) 1.94-2.09 (m, 2H) 2.17 (s, 2H) 2.97 (t, J=11.44 Hz, 1H) 3.13 (q, J=6.72 Hz, 2H) 3.24 (t, J=11.77 Hz, 1H) 3.90 (dd, J=7.30, 3.53 Hz, 1H) 4.26 (d, J=13.47 Hz, 1H) 4.34-4.47 (m, 2H) 4.64 (d, J=13.38 Hz, 1H) 7.06 (d, J=8.38 Hz, 2H) 7.12-7.18 (m, 1H) 7.20-7.34 (m, 3H) 7.44 (d, J=2.07 Hz, 1H); [M+H]$^+$ 562.3.

N-(1-{[5-(4-Chlorophenyl)-1-(2,4-dichlorophenyl)-4-methyl-1H-pyrazol-3-yl]carbonyl}piperidin-4-yl) methanesulfonamide 1-{[5-(4-Chlorophenyl)-1-(2,4-dichlorophenyl)-4-methyl-1H-pyrazol-3-yl]carbonyl}piperidin-4-amine (20 mg, 0.043 mmol, 1 eq.), triethylamine (0.02 mL, 0.129 mmol, 3 eq.), and the methanesulfonyl chloride (0.007 mL, 0.086 mmol, 2 eq.) were stirred in dichloromethane (2 mL) for 16 h. The reaction was concentrated in vacuo. The crude material was purified by column chromatography 0-100% ethyl acetate/hexanes to yield 17 mg (74%) of desired product. $^1$H NMR (300 MHz, CHLOROFORM-d) δ ppm 1.60 (dd, J=14.60, 7.06 Hz, 2H) 2.05-2.36 (m, 5H) 2.93-3.10 (m, 3H) 3.35-3.76 (m, 2H) 4.45 (br. s., 2H) 4.71 (br. s., 1H) 7.07 (d, J=7.91 Hz, 2H) 7.15 (d, J=7.72 Hz, 1H) 7.20-7.35 (m, 3H) 7.45 (s, 1H); [M+H]$^+$ 541.3.

General Procedure for Making Ureas from 1-{[5-(4-chlorophenyl)-1-(2,4-dichlorophenyl)-4-methyl-1H-pyrazol-3-yl]carbonyl}-4-phenylpiperidin-4-amine.

1-{[5-(4-Chlorophenyl)-1-(2,4-dichlorophenyl)-4-methyl-1H-pyrazol-3-yl]carbonyl}-4-phenylpiperidin-4-amine (26.1 mg, 0.048 mmol, 1 eq.), triethylamine (0.02 mL, 0.145 mmol, 3 eq.), and the appropriate isocyanate (0.073 mmol, 1.5 eq.) were stirred in THF (2 mL) for 16 h. The reaction was concentrated in vacuo. The crude material was purified by column chromatography 0-100% ethyl acetate/hexanes to yield desired product.

1-(1-{[5-(4-chlorophenyl)-1-(2,4-dichlorophenyl)-4-methyl-1H-pyrazol-3-yl]carbonyl}-4-phenylpiperidin-4-yl)-3-hexylurea. Reaction proceeded in 72% yield. $^1$H NMR (300 MHz, CHLOROFORM-d) δ ppm 0.84 (t, J=6.78 Hz, 3H), 1.04-1.38 (m, 8H), 1.95-2.17 (m, 3H), 2.17-2.25 (m, 3H), 2.51 (br s, 1H), 2.90-3.11 (m, 2H), 3.2 (br s, 1H), 3.55 (br s, 1H), 4.28 (d, J=13.56 Hz, 1H), 4.48-4.65 (m, 2H), 5.18-5.38 (m, 1H), 6.96-7.51 (m, 12H); [M–H]$^-$ 666.8.

1-(1-{[5-(4-chlorophenyl)-1-(2,4-dichlorophenyl)-4-methyl-1H-pyrazol-3-yl]carbonyl}-4-phenylpiperidin-4-yl)-3-(propan-2-yl)urea. Reaction proceeded in 73% yield. $^1$H NMR (300 MHz, CHLOROFORM-d) δ ppm 0.82-1.03 (m, 6H), 1.94-2.24 (m, 6H), 2.46 (d, J=13.47 Hz, 1H), 3.26 (t, J=11.26 Hz, 1H), 3.56 (t, J=12.10 Hz, 1H), 3.68-3.85 (m, 1H), 4.16-4.37 (m, 2H), 4.59 (d, J=13.47 Hz, 1H), 5.05 (s, 1H), 6.94-7.49 (m, 12H); [M+H]$^+$ 624.7.

1-(1-{[5-(4-chlorophenyl)-1-(2,4-dichlorophenyl)-4-methyl-1H-pyrazol-3-yl]carbonyl}-4-phenylpiperidin-4-yl)-3-ethylurea. Reaction proceeded in 73% yield. $^1$H NMR (300 MHz, CHLOROFORM-d) δ ppm 0.78-1.04 (m, 3H), 1.92-2.25 (m, 6H), 2.51 (d, J=13.56 Hz, 1H), 2.98-3.15 (m, 2H), 3.24 (br s, 1H), 3.55 (br s, 1H), 4.29 (br s, 1H), 4.44-4.68 (m, 2H), 5.23 (s, 1H), 6.90-7.49 (m, 12H); [M+H]$^+$ 610.1.

1-(1-{[5-(4-chlorophenyl)-1-(2,4-dichlorophenyl)-4-methyl-1H-pyrazol-3-yl]carbonyl}-4-phenylpiperidin-4-yl)-3-propylurea. Reaction proceeded in 71% yield. $^1$H NMR (300 MHz, CHLOROFORM-d) δ ppm 0.74 (t, J=7.39 Hz, 3H), 1.21-1.40 (m, 2H), 2.05-2.29 (m, 6H), 2.35 (br s, 1H), 3.02 (q, J=6.72 Hz, 2H), 3.28 (br s, 1H), 3.57 (br s, 1H), 4.0 (t, J=5.27 Hz, 1H), 4.34 (d, J=13.66 Hz, 1H), 4.63 (d, J=14.32 Hz, 1H), 4.74 (s, 1H), 7.00-7.54 (m, 12H); [M+H]$^+$ 624.8.

3-(1-{[5-(4-chlorophenyl)-1-(2,4-dichlorophenyl)-4-methyl-1H-pyrazol-3-yl]carbonyl}-4-phenylpiperidin-4-yl)-1-cyclohexylurea. Reaction proceeded in 69% yield. $^1$H NMR (300 MHz, CHLOROFORM-d) δ ppm 0.78-0.98 (m, 2H), 1.06 (d, J=9.89 Hz, 1H), 1.16-1.35 (m, 2H), 1.50 (d, J=8.76 Hz, 3H), 1.73 (d, J=10.83 Hz, 2H), 2.00-2.27 (m, 6H), 2.43 (d, J=13.56 Hz), 3.26 (br s, 1H), 3.37-3.66 (m, 2H), 4.15-4.40 (m, 2H), 4.62 (br s, 1H), 4.99 (s, 1H), 6.90-7.55 (m, 12H); [M+H]$^+$ 664.9.

3-butyl-1-(1-{[5-(4-chlorophenyl)-1-(2,4-dichlorophenyl)-4-methyl-1H-pyrazol-3-yl]carbonyl}-4-phenylpiperidin-4-yl)urea. Reaction proceeded in 71% yield. $^1$H NMR (300 MHz, CHLOROFORM-d) δ ppm 0.76-0.86 (m, 3H), 1.08-1.21 (m, 2H), 1.28 (dq, J=14.40, 7.10 Hz, 2H), 1.94-2.26 (m, 6H), 2.50 (d, J=13.47 Hz, 1H), 3.04 (q, J=6.56 Hz, 2H), 3.15-3.32 (m, 1H), 3.55 (t, J=12.15 Hz, 1H), 4.27 (d, J=13.56 Hz, 1H), 4.48-4.74 (m, 2H), 5.33 (s, 1H), 6.98-7.49 (m, 12H); [M+H]+ 638.6.

4-C-5-(4-chlorophenyl)-1-(2,4-dichlorophenyl)-4-methyl-1H-pyrazole-3-piperidine-1,4-diamido 1-N-tert-butyl-4-C-5-(4-chlorophenyl)-1-(2,4-dichlorophenyl)-4-methyl-1H-pyrazole-3-piperidine-1,4-diamido (33 mg, 0.059 mmol, 1 eq) was stirred in dichloromethane (2 mL) and trifluoroacetic acid (2 mL) overnight. The mixture was concentrated in vacuo. The crude reaction material was then purified by silica gel column chromatography using 0-100% CMA 80/ethyl acetate to yield pure desired product (24 mg, 81%). $^1$H NMR (300 MHz, CHLOROFORM-d) δ ppm 1.41-1.60 (m, 2H), 1.99-2.12 (m, 2H), 2.37 (s, 3H), 3.01 (t, J=11.77 Hz, 2H), 3.94 (d, J=13.09 Hz, 2H), 4.03-4.24 (m, 1H), 4.65 (br s, 2H), 6.90 (d, J=7.91 Hz, 1H), 7.06 (d, J=8.38 Hz, 2H), 7.22-7.37 (m, 4H), 7.43 (s, 1H); [M+H]+ 506.4.

Example 2

Analysis

All compounds were characterized by H$^1$ NMR and evaluated using a calcium mobilization assay. Each compound was pharmacologically characterized using a functional fluorescent CB1 activated Gαq16-coupled intracellular calcium mobilization assay in CHO-K1 cells as has been previously described and apparent affinity (Ke) values were determined. See Zhang et al., *J. Med. Chem.* 2010, 53, 7048, which is incorporated herein by reference. Further characterization of select compounds was performed using radioligand displacement of [3H]1 and equilibrium dissociation constant (Ki) values were determined. Selectivity of these compounds at CB1 versus CB2 was also determined by obtaining Ki values at either receptor using displacement of [3H]CP55940 in membranes of CHO-K1 cells over-expressing either receptor. Data reported are average values from 3-6 measurements.

TABLE 1

Alkyl pyridinium salts and N-oxide derivatives via Scheme 1

| R | Ke CB1 (μM) |
|---|---|
| 4-pyridyl | 0.117 |
| 1-methyl-4-pyridinium iodide | >10 |
| pyridine 4-N-oxide | 1.39 |
| 6-methyl-3-pyridyl | 0.384 |
| 1,6-dimethyl-3-pyridinium iodide | 8.41 |
| 6-methyl-3-pyridyl N-oxide | 1.20 |
| 5-methyl-2-pyridyl | 0.980 |
| 1,5-dimethyl-2-pyridinium iodide | 8.59 |
| 5-methyl-2-pyridyl N-oxide | 4.58 |

The pyridinium compounds were charged analogs of a reported methylpyridine amide. See International Patent Appl. No. WO 2007/010217 to Jones et al., which is incorporated herein by reference. To date, only limited activity has been observed with alkyl pyridinium salts and pyridine N-oxides (Table 1). The parent pyridines of Table 1 are more potent than their alkyl pyridinium salt or N-oxide analogues in all cases. All pyridinium salt analogues made to date have apparent affinity (Ke) values of greater than 8 μM against CB1. The pyridine N-oxides demonstrated modest activity, with two pyridine N-oxides in Table 1 having Ke values less than 2 μM, making them of some interest.

TABLE 2

Sulfonamide and sulfamide derivatives via Scheme 2

| R | Ke CB1 (μM) | TPSA |
|---|---|---|
| (structure: alkyl chain with NHSO₂Me) | 0.207 | 101 |
| (structure: alkyl chain with NHSO₂NH₂) | 0.304 | 127 |
| (structure: cyclohexyl-NH₂) | >10 | 73 |
| (structure: cyclohexyl-NHSO₂Me) | >10 | 101 |
| (structure: cyclohexyl-NHSO₂NH₂) | 9.43 | 127 |

TABLE 2-continued

Sulfonamide and sulfamide derivatives via Scheme 2

| R | Ke CB1 (μM) | TPSA |
|---|---|---|
| (structure: cyclohexyl-CH₂-cyclohexyl-CH₂NH₂) [a] | 3.76 | 73 |
| (structure: cyclohexyl-CH₂-cyclohexyl-CH₂NHSO₂Me) [a] | 0.113 | 101 |
| (structure: cyclohexyl-CH₂-cyclohexyl-CH₂NHSO₂NH₂) [a] | 0.106 | 127 |
| (structure: cyclohexyl-CH₂-cyclohexyl-CH₂NHSO₂Me) [b] | 0.030 | 101 |
| (structure: cyclohexyl-CH₂-cyclohexyl-CH₂NHSO₂NH₂) [b] | 0.093 | 127 |

TABLE 2-continued

Sulfonamide and sulfamide derivatives via Scheme 2

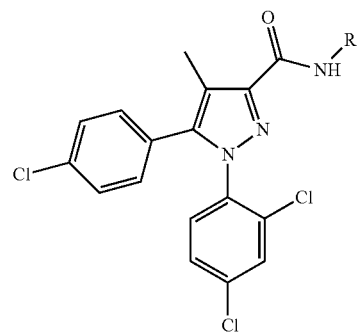

| R | Ke CB1 (μM) | TPSA |
|---|---|---|
| 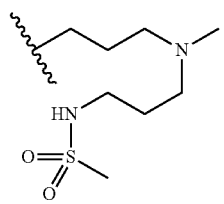 [SMILES: *CCCN(C)CCCNS(C)(=O)=O] | 5.34 | 105 |
| 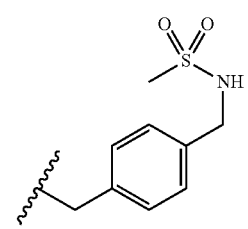 [SMILES: *Cc1ccc(CNS(C)(=O)=O)cc1] | 2.93 | 101 |
| 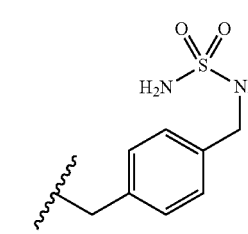 | 0.376 | 127 |
| 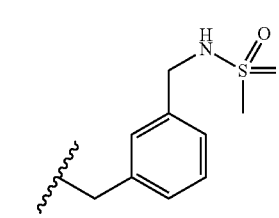 | 2.83 | 101 |
| 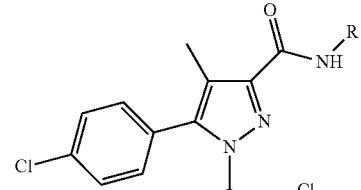 | 4.20 | 127 |

[a]Compounds isolated are approximately 1:1 mixture of cis and trans isomers
[b]Compounds are 7:1 mixture of cis/trans isomers The initial CB1 antagonists with high TPSAs, the first two entries in Table 2 (a sulfonamide and sulfamide) were both active at the CB1 receptor and have significantly higher TPSAs than rimonabant (rimonabant's TPSA is 50 and the TPSAs for the first two compounds in Table 2 are 101 and 127 respectively). With these compounds in hand, attempts were made to improve potency for these CB1 receptor antagonists while maintaining high TPSAs. Constrained analogues were targeted in hopes of improving potency. The initial constrained analogues had little or no activity. Therefore, compounds with longer spacers (X, Scheme 2), were targeted. These compounds, as a 1:1 cis/trans mixture, were functionally potent (Ke~100 nM) and bound CB1 with high affinity (Ki~10 nM). The following two entries in the table, which are compounds enriched in the cis isomer (cis:trans~7:1) were demonstrated to be slightly more potent. The following entry suggested that basic spacer groups with sulfonamides were not tolerated. Also, basic groups at the terminus of the linker were not tolerated, based on data for NH$_2$-terminal compounds. The final four compounds in Table 2 were prepared to study the effect of in the nature of the spacer on activity. In certain cases, aromatic groups used as spacers were deemed detrimental for CB1 activity.

Select compounds were chosen for further study in radioligand displacement assays using radiolabeled rimonobant, SR141716 ([$^3$H]1). See Table 3. Several of these compounds demonstrated excellent Ki values in the low nM range, with one having a Ki of 8 nM. Selectivity against the CB2 receptor was determined by comparing the compound displacement of radiolabeled CP55940, which is a cannabinoid known to act as a full agonist at both CB1 and CB2 receptors. In general, tested compounds were selective for CB1 over CB2.

TABLE 3

Radioligand displacement data for select N-oxide, sulfamide, and sulfonamide compounds

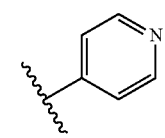 [SMILES: *c1ccncc1]

| R | Ki(μM) CB1 SR141716 | Ki(μM) CB1 CP55940 | Ki(μM) CB2 CP55940 | CB2:CB1 CP55940 |
|---|---|---|---|---|
| 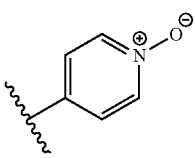 [SMILES: *c1cc[n+]([O-])cc1] | 0.013 | 0.056 | 1.74 | 31 |
|  | 0.061 | 0.294 | 4.52 | 15 |

TABLE 3-continued

Radioligand displacement data for select N-oxide, sulfamide, and sulfonamide compounds

[Structure: pyrazole core with 4-methyl, 5-(4-chlorophenyl), 1-(2,4-dichlorophenyl), 3-carboxamide NH-R]

| R | Ki(μM) CB1 SR141716 | Ki(μM) CB1 CP55940 | Ki(μM) CB2 CP55940 | CB2:CB1 CP55940 |
|---|---|---|---|---|
| 2-methylpyridin-5-yl | 0.026 | 0.102 | 4.01 | 39 |
| 1,2-dimethylpyridinium-5-yl I⊖ | 0.786 | 1.698 | 2.27 | 1.3 |
| –(CH2)n–NH–S(O)2–CH3 [a] | 0.060 | 0.158 | 0.78 | 4.9 |
| –(CH2)n–NH–S(O)2–NH2 [a] | 0.020 | 0.049 | 1.01 | 21 |
| cyclohexyl-CH2-NH-S(O)2-CH3 [b] | 0.011 | 0.055 | 0.90 | 16 |
| cyclohexyl-CH2-NH-S(O)2-NH2 (H2N-) [b] | 0.021 | 0.135 | 2.31 | 17 |
| cyclohexyl-CH2-NH-S(O)2-CH3 | 0.008 | 0.036 | 0.96 | 27 |
| cyclohexyl-CH2-NH-S(O)2-NH2 (H2N-) | 0.015 | 0.107 | 1.79 | 17 |

[a]Compounds isolated are approximately 1:1 mixture of cis and trans isomers
[b]Compounds are 7:1 mixture of cis/trans isomers Charged compounds generally showed poor activity in the calcium flux assay. However, the second compound of Table 3 demonstrated good affinity of for CB1 versus $^3$H-SR141716 (Ki of 61 nM) in contrast to its Ke=1.39 μM for calcium flux. An explanation for this disparity could be the different levels of access to the receptor by the ligand. Affinity was determined in a disrupted membrane assay while the functional calcium flux assay was conducted using intact cells. If, as reported for CB1 and CB2 receptor, this cannabinoid ligand enters the CB1 receptor not from the extracellular receptor surface but rather from the intra-membrane lipid milieu, then the charged nature of the pyridinium analogs might preclude its required penetration past the charged phosphate head groups of the membrane lipid bilayer. This lack of penetration would inhibit the functional assay but not the binding assay where the membrane is no longer intact.

Certain other piperidine-containing compounds were evaluated, with data shown below in Table 4.

TABLE 4

Radioligand displacement data for select piperidine-containing compounds

| R | X | Y | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (apical to basal) |
|---|---|---|---|---|---|---|---|---|
| Cl | phenyl | C(O)NH₂ | 0.45 | 0.44 | 3.44 | 5504 | 1600.0 | 8.1 ± 11.5 |
| Cl | NHC₂H₅ | C(O)NH₂ | 91.00 | 34.6 | 78.4 | 2217 | | |
| N(CH₃)₂ | phenyl | OH | 679.00 | 72.5 | 384 | 400 | 1.0 | |
| Br | phenyl | CONH₂ | 2.40 | 2.67 | 14.5 | 3282 | 226.3 | |
| Br | phenyl | OH | 36.96 | | | | | |
| Cl | phenyl | NHC(O)O(t-butyl) | 20.23 | 6.02 | 42.3 | 2110 | 48.9 | <1% |
| Cl | phenyl | NH2 | 485.00 | 30.5 | 104 | 1127 | 10.8 | |
| Cl | phenyl | NHC(O)CH₃ | 201.00 | 13.7 | 62.6 | 214 | 3.4 | |
| Cl | phenyl | NHSO₂CH₃ | 3.55 | 3.28 | 7.27 | 41 | 5.6 | 3.14 ± 0.89 |
| Cl | phenyl | NHC(O)NH(t-butyl) | 2.40 | 18.1 | 47.1 | 20000 | 424.6 | <1% |
| CN | phenyl | OH | 907.00 | | | | | |
| Cl | phenyl | OH | 20.12 | 9.63 | 67.4 | 831 | 12.3 | |
| Cl | phenyl | C(O)NH(t-butyl) | 49.6 | | 19.9 | 8389 | 421.6 | <1% |
| Cl | phenyl | NHC(O)NH (C₆H₁₃) | 0.47 | | 38.8 | 2414 | 62.2 | |
| Cl | phenyl | NHC(O)NH CH(CH₃)₂ | 0.71 | | 13.5 | 4914 | 364.0 | <1% |
| Cl | phenyl | NHC(O)NH CH₂CH₃ | 10.85 | | 15 | 182 | 12.1 | |
| Cl | phenyl | NHC(O)NH C₃H₇ | 0.41 | | 7.57 | 293 | 38.7 | |
| Cl | phenyl | NHC(O)NH (cyclohexyl) | 17.47 | | 792 | 20000 | 25.3 | |
| Cl | phenyl | NHC(O)NH C₄H₉ | 0.41 | | 15.5 | 2760 | 178.1 | |
| Cl | H | NHC(O)O(t-butyl) | 209 | | | | | |
| Cl | H | NH₂ | 1920 | | | | | |
| Cl | H | NHC(O)NH CH(CH₃)₂ | 608 | | | | | |
| Cl | H | NHC(O)NH C₃H₇ | 546 | | | | | |
| Cl | H | NHC(O)NH C₄H₉ | 395 | | | | | |
| Cl | H | NHS(O)₂CH₃ | 146 | | | | | |

Piperidine-containing urea and carbamate compounds were also evaluated, with data shown below in Table 5.

TABLE 5

Radioligand displacement data for N-piperidine-containing compounds

| R | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement |
|---|---|---|---|---|---|
| $NH_2$ | 4097 | | | | |
| $NHC_2H_5$ | 20.47 | | 167.35 | 13218.5 | 79.0 |
| NH(isopropyl) | 16.72 | | 97.855 | 17194.5 | 175.7 |
| NH(n-propyl) | 66.5 | | | | |
| NH(n-butyl) | 60 | | 148.55 | >20,000 | |
| $OC_2H_5$ | 28.6 | | 14.64 | 8067.5 | 551.1 |
| O-isopropyl | 20 | | | | |
| $OC_4H_9$ | 88 | | | | |
| $OCH_3$ | 59 | | | | |
| O-n-propyl | 12 | | | | |

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:
1. A compound according to the structure:

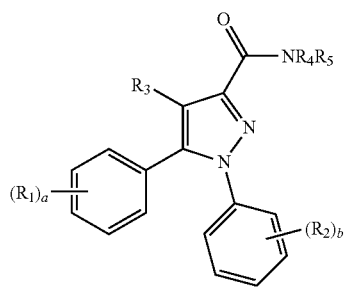

wherein:
each $R_1$ and $R_2$ is a substituent independently selected from the group consisting of Cl, F, Br, OH, optionally substituted C1-10 alkyl, optionally substituted C1-10 alkoxy, optionally substituted C2-4 alkenyl, optionally substituted C2-4 alkynyl, $NR_{10}R_{11}$, $NHCOR_{10}$, $NHCO_2R_{10}$, $CH_2OR_{10}$, $CONR_{10}R_{11}$, $CO_2R_{10}$, CN, $CF_3$, $NO_2$, $N_3$, C1-3 alkylthio, $R_{10}SO$, $R_{10}SO_2$, $CF_3S$, and $CF_3SO_2$;
$R_3$ is H or C1-3 alkyl;
$R_4$ and $R_5$ taken together form a piperidine ring with the N to which they are attached, which is substituted at the 4 position with at least one substituent selected from the group consisting of $NR_{10}R_{11}$, $NR_{10}COR_{11}$, $NR_{10}SO_2R_{11}$, $NHCONR_{10}R_{11}$, $NR_{10}COOR_{11}$; and $CONR_{10}R_{11}$,
$R_{10}$ and $R_{11}$ are independently selected from H and C1-10 alkyl;
and a and b are each independently integers from 0 to 5
or a pharmaceutically acceptable ester, amide, salt, solvate, prodrug, or stereoisomer thereof.

2. The compound of claim 1, wherein a is 1 and the $R_1$ substituent is at the para position and b is 2 and the $R_2$ substituents are at the ortho and para positions.

3. The compound of claim 2, wherein $R_1$ and both $R_2$ substituents are Cl.

4. The compound of claim 1, wherein $R_3$ is $CH_3$.

5. The compound of claim 1, wherein the compound comprises one or more chiral centers.

6. The compound of claim 1, selected from the group consisting of:
1-{[5-4-chlorophenyl)-1-(2,4-dichlorophenyl)-4-methyl-1H-pyrazol-3-yl]carbonyl}-4-phenylpiperidine-4-carboxamide;
1-{[5-4-chlorophenyl)-1-(2,4-dichlorophenyl)-4-methyl-1H-pyrazol-3-yl]carbonyl}-4-(ethylamino)piperidine-4-carboxamide;
1-{[5-(4-bromophenyl)-1-(2,4-dichlorophenyl)-4-methyl-1H-pyrazol-3-yl]carbonyl}-4-phenylpiperidine-4-carboxamide;
tert-Butyl N-(1-{[5-(4-chlorophenyl)-1-(2,4-dichlorophenyl)-4-methyl-1H-pyrazol-3-yl]carbonyl}-4-phenylpiperidin-4-yl)carbamate;
1-{[5-(4-chlorophenyl)-1-(2,4-dichlorophenyl)-4-methyl-1H-pyrazol-3-yl]carbonyl}-4-phenylpiperidin-4-amine;
N-(1-{[5-(4-chlorophenyl)-1-(2,4-dichlorophenyl)-4-methyl-1H-pyrazol-3-yl]carbonyl}-4-phenylpiperidin-4-yl)acetamide;
N-(1-{[5-(4-chlorophenyl)-1-(2,4-dichlorophenyl)-4-methyl-1H-pyrazol-3-yl]carbonyl}-4-phenylpiperidin-4-yl)methanesulfonamide;
3-tert-butyl-1-(1-{[5-(4-chlorophenyl)-1-(2,4-dichlorophenyl)-4-methyl-1H-pyrazol-3-yl]carbonyl}-4-phenylpiperidin-4-yl)urea;
1-N-tert-butyl-4-C-5-(4-chlorophenyl)-1-(2,4-dichlorophenyl)-4-methyl-1H-pyrazole-3-piperidine-1,4-diamido;
tert-butyl N-(1-{[5-(4-chlorophenyl)-1-(2,4-dichlorophenyl)-4-methyl-1H-pyrazol-3-yl]carbonyl}piperidin-4-yl)carbamate;
1-{[5-(4-chlorophenyl)-1-(2,4-dichlorophenyl)-4-methyl-1H-pyrazol-3-yl]carbonyl}piperidin-4-amine;
1-(1-{[5-(4-chlorophenyl)-1-(2,4-dichlorophenyl)-4-methyl-1H-pyrazol-3-yl]carbonyl}piperidin-4-yl)-3-(propan-2-yl)urea;
1-(1-{[5-(4-chlorophenyl)-1-(2,4-dichlorophenyl)-4-methyl-1H-pyrazol-3-yl]carbonyl}piperidin-4-yl)-3-propylurea;
3-butyl-1-(1-{[5-(4-chlorophenyl)-1-(2,4-dichlorophenyl)-4-methyl-1H-pyrazol-3-yl]carbonyl}piperidin-4-yl)urea;

N-(1-{[5-(4-chlorophenyl)-1-(2,4-dichlorophenyl)-4-methyl-1H-pyrazol-3-yl]carbonyl}piperidin-4-yl)methanesulfonamide;

1-(1-{[5-(4-chlorophenyl)-1-(2,4-dichlorophenyl)-4-methyl-1H-pyrazol-3-yl]carbonyl}-4-phenylpiperidin-4-yl)-3-hexylurea;

1-(1-{[5-(4-chlorophenyl)-1-(2,4-dichlorophenyl)-4-methyl-1H-pyrazol-3-yl]carbonyl}-4-phenylpiperidin-4-yl)-3-(propan-2-yl)urea;

1-(1-{[5-(4-chlorophenyl)-1-(2,4-dichlorophenyl)-4-methyl-1H-pyrazol-3-yl]carbonyl}-4-phenylpiperidin-4-yl)-3-ethylurea;

1-(1-{[5-(4-chlorophenyl)-1-(2,4-dichlorophenyl)-4-methyl-1H-pyrazol-3-yl]carbonyl}-4-phenylpiperidin-4-yl)-3-propylurea;

3-(1-{[5-(4-chlorophenyl)-1-(2,4-dichlorophenyl)-4-methyl-1H-pyrazol-3-yl]carbonyl}-4-phenylpiperidin-4-yl)-1-cyclohexylurea;

3-butyl-1-(1-{[5-(4-chlorophenyl)-1-(2,4-dichlorophenyl)-4-methyl-1H-pyrazol-3-yl]carbonyl}-4-phenylpiperidin-4-yl)urea;

4-C-5-(4-chlorophenyl)-1-(2,4-dichlorophenyl)-4-methyl-1H-pyrazole-3-piperidine-1,4-diamido;

4-C-5-(4-chlorophenyl)-1-(2,4-dichlorophenyl)-4-methyl-1H-pyrazole-3-1-N-ethylpiperidine-1,4-diamido;

4-C-5-(4-chlorophenyl)-1-(2,4-dichlorophenyl)-4-methyl-1H-pyrazole-3-1-N-(propan-2-yl)piperidine-1,4-diamido;

4-C-5-(4-chlorophenyl)-1-(2,4-dichlorophenyl)-4-methyl-1H-pyrazole-3-1-N-propylpiperidine-1,4-diamido;

1-N-butyl-4-C-5-(4-chlorophenyl)-1-(2,4-dichlorophenyl)-4-methyl-1H-pyrazole-3-piperidine-1,4-diamido;

N-(tert-butyl)-1-(5-(4-chlorophenyl)-1-(2,4-dichlorophenyl)-4-methyl-1H-pyrazole-3-carbonyl)-4-phenylpiperidine-4-carboxamide;

or a pharmaceutically acceptable ester, amide, salt, solvate, prodrug, or stereoisomer thereof.

7. A method for treating or delaying the progression of disorders that are alleviated by antagonizing the CB1 receptor, the method comprising administering a compound according to claim 1, wherein the disorder is selected from the group consisting of obesity, liver diseases, diabetes, pain, inflammation, and dyslipidemia.

8. A pharmaceutical composition, comprising the compound of claim 1 and one or more pharmaceutically acceptable carriers.

* * * * *